United States Patent
Horiuchi et al.

(10) Patent No.: US 10,971,174 B2
(45) Date of Patent: Apr. 6, 2021

(54) INFORMATION PROCESSING APPARATUS, INFORMATION PROCESSING METHOD, AND NON-TRANSITORY COMPUTER READABLE RECORDING MEDIUM

(71) Applicant: OLYMPUS CORPORATION, Tokyo (JP)

(72) Inventors: Kazuhito Horiuchi, Hachioji (JP); Nobuyuki Watanabe, Yokohama (JP); Yoshioki Kaneko, Hachioji (JP); Hidetoshi Nishimura, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 196 days.

(21) Appl. No.: 16/411,540

(22) Filed: May 14, 2019

(65) Prior Publication Data

US 2019/0355382 A1    Nov. 21, 2019

(30) Foreign Application Priority Data

May 17, 2018 (JP) .............................. JP2018-095520
May 10, 2019 (JP) .............................. JP2019-090107

(51) Int. Cl.
*G10L 25/78* (2013.01)
*G10L 15/26* (2006.01)
(Continued)

(52) U.S. Cl.
CPC .......... *G10L 25/78* (2013.01); *A61B 1/00006* (2013.01); *A61B 1/00009* (2013.01);
(Continued)

(58) Field of Classification Search
CPC ......... G10L 25/78; G10L 15/26; G06F 3/013; G06F 3/167; A61B 1/00041; A61B 1/05;
(Continued)

(56) References Cited

U.S. PATENT DOCUMENTS

2007/0226189 A1*  9/2007  Piekos ................. G06F 3/0481
2015/0379333 A1* 12/2015  Ingram ............ H04N 5/232933
                                                              348/46

FOREIGN PATENT DOCUMENTS

JP        4282343 B2     6/2009
JP     2016-181245 A    10/2016

OTHER PUBLICATIONS

English Abstract of JP 2004-259198 A, dated Sep. 4, 2016.

* cited by examiner

*Primary Examiner* — Asghar H Bilgrami
(74) *Attorney, Agent, or Firm* — Scully, Scott, Murphy & Presser, P.C.

(57) ABSTRACT

An information-processing apparatus includes a display displaying an image; a memory recording voice data having a voice pronounced at each of plural observation points of the image; a gaze detector generating gaze data by detecting a gaze of a user; a voice input device generating voice data associated with a time axis identical to that of the gaze data by receiving a voice of the user; and a processor to analyze a attention period where a attention degree of the gaze to each of the plural observation points is a predetermined value or greater, based on the gaze data, set a period where the voice is pronounced with respect to the voice data as an important voice period, based on the voice data, and generate calibration data based on a time lag between the attention period and the important voice period.

20 Claims, 29 Drawing Sheets

(51) Int. Cl.
*G06F 3/01* (2006.01)
*G06F 3/16* (2006.01)
*A61B 1/00* (2006.01)
*G02B 25/00* (2006.01)
*A61B 1/05* (2006.01)
*G02B 27/00* (2006.01)
*G02B 21/36* (2006.01)

(52) U.S. Cl.
CPC ............ *A61B 1/00041* (2013.01); *A61B 1/05* (2013.01); *G02B 21/365* (2013.01); *G02B 25/001* (2013.01); *G06F 3/013* (2013.01); *G06F 3/167* (2013.01); *G10L 15/26* (2013.01)

(58) Field of Classification Search
CPC ............ A61B 1/00006; A61B 1/00009; G02B 25/001; G02B 21/365; G02B 27/0093
See application file for complete search history.

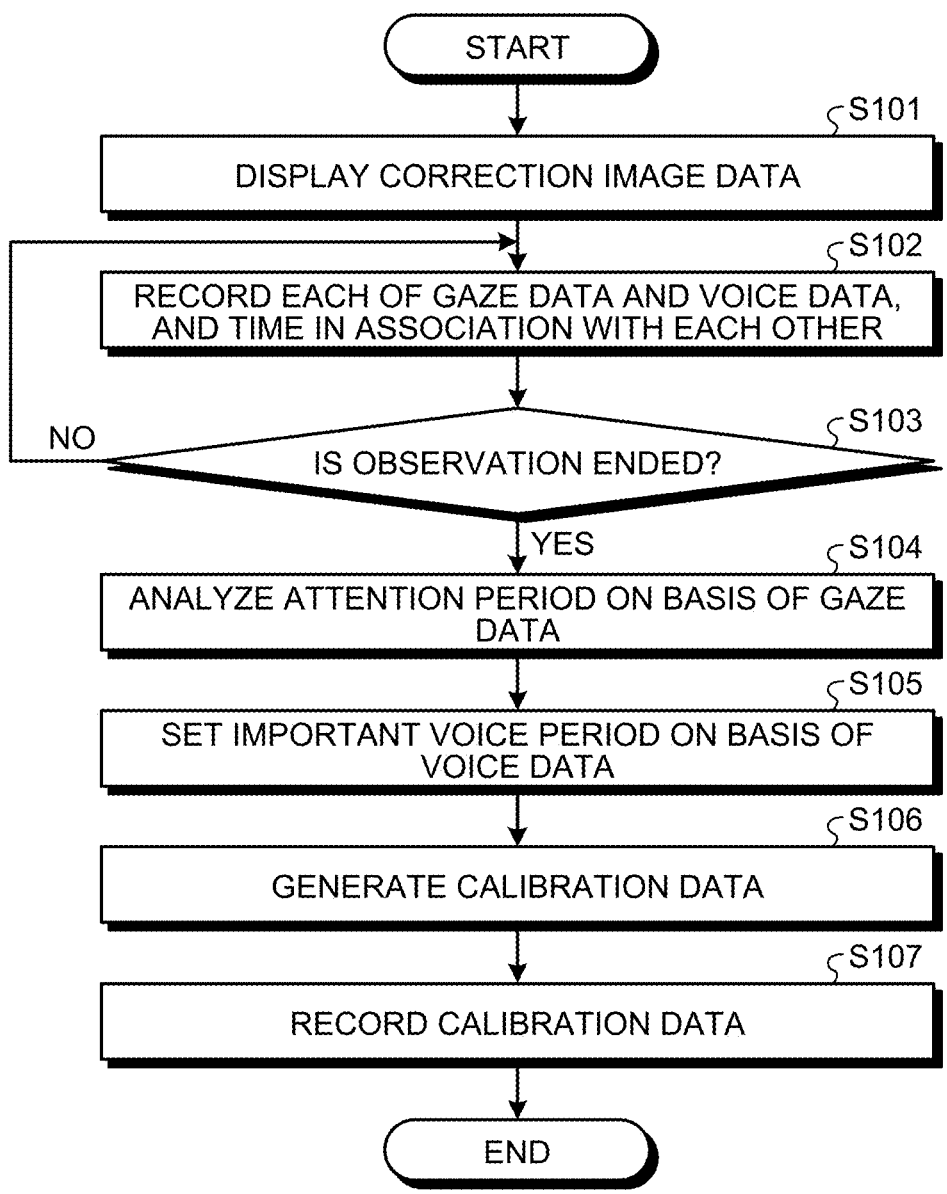

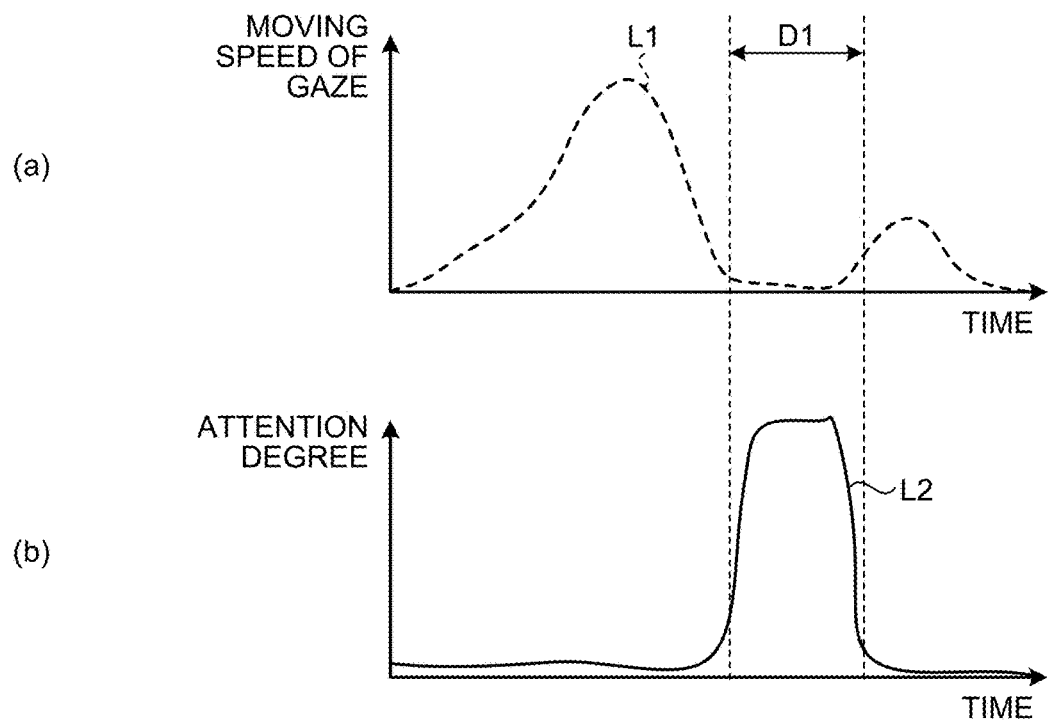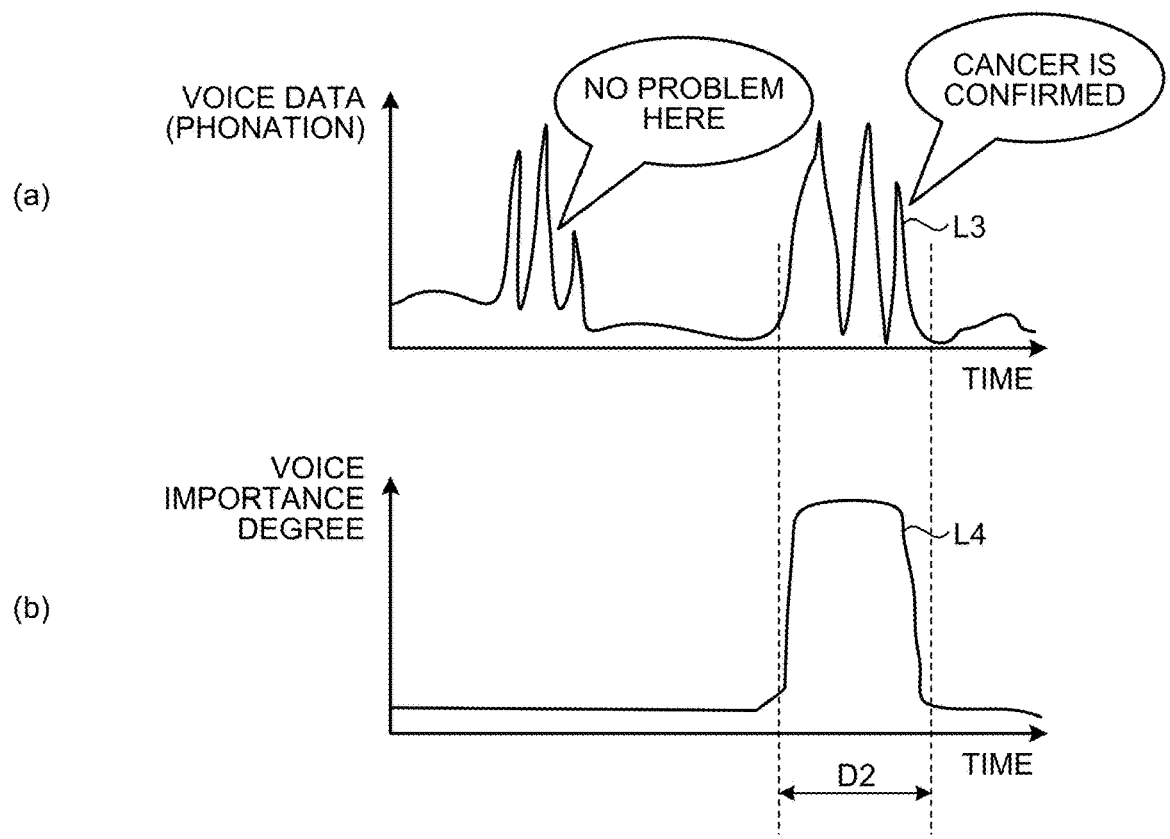

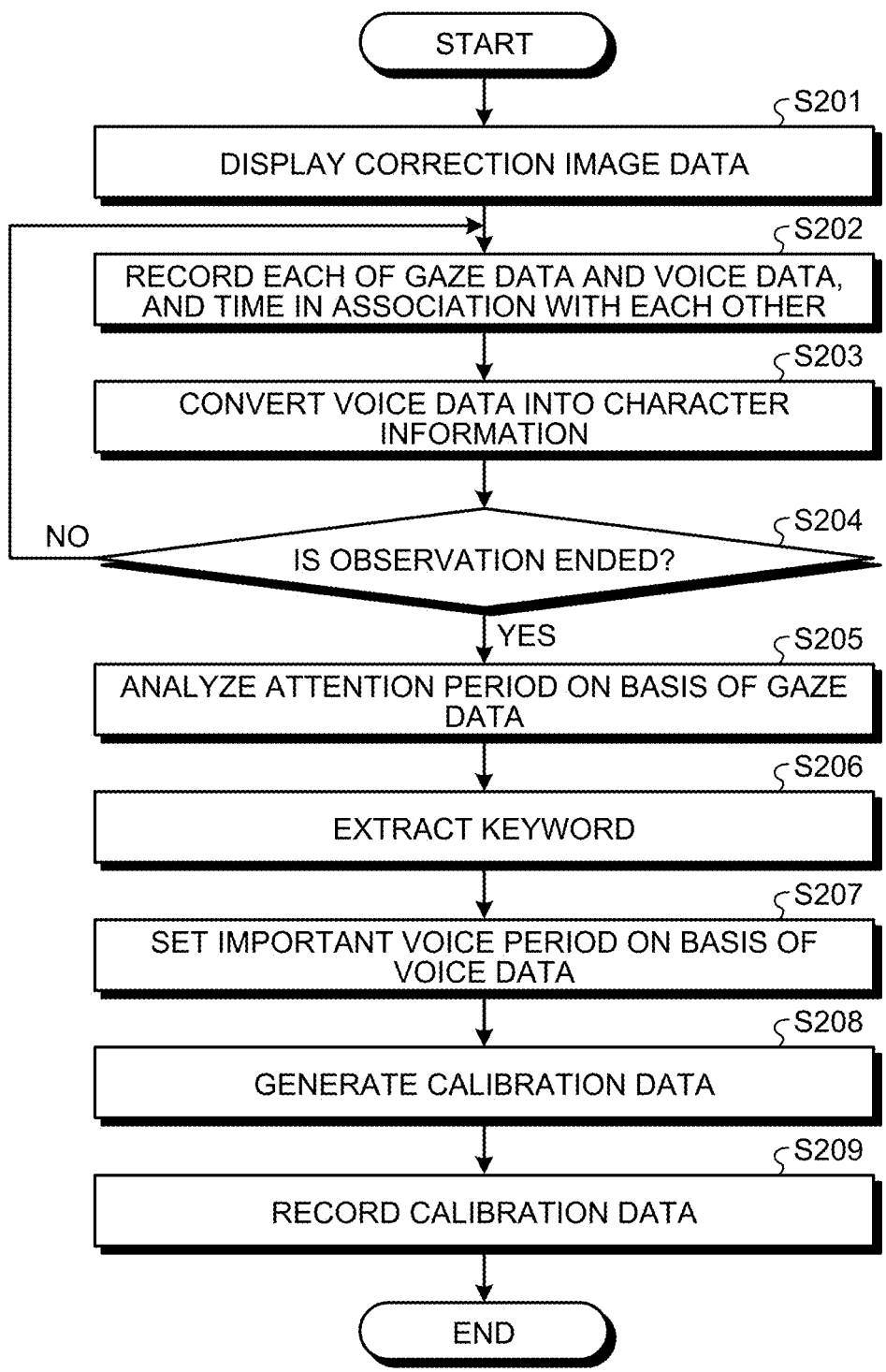

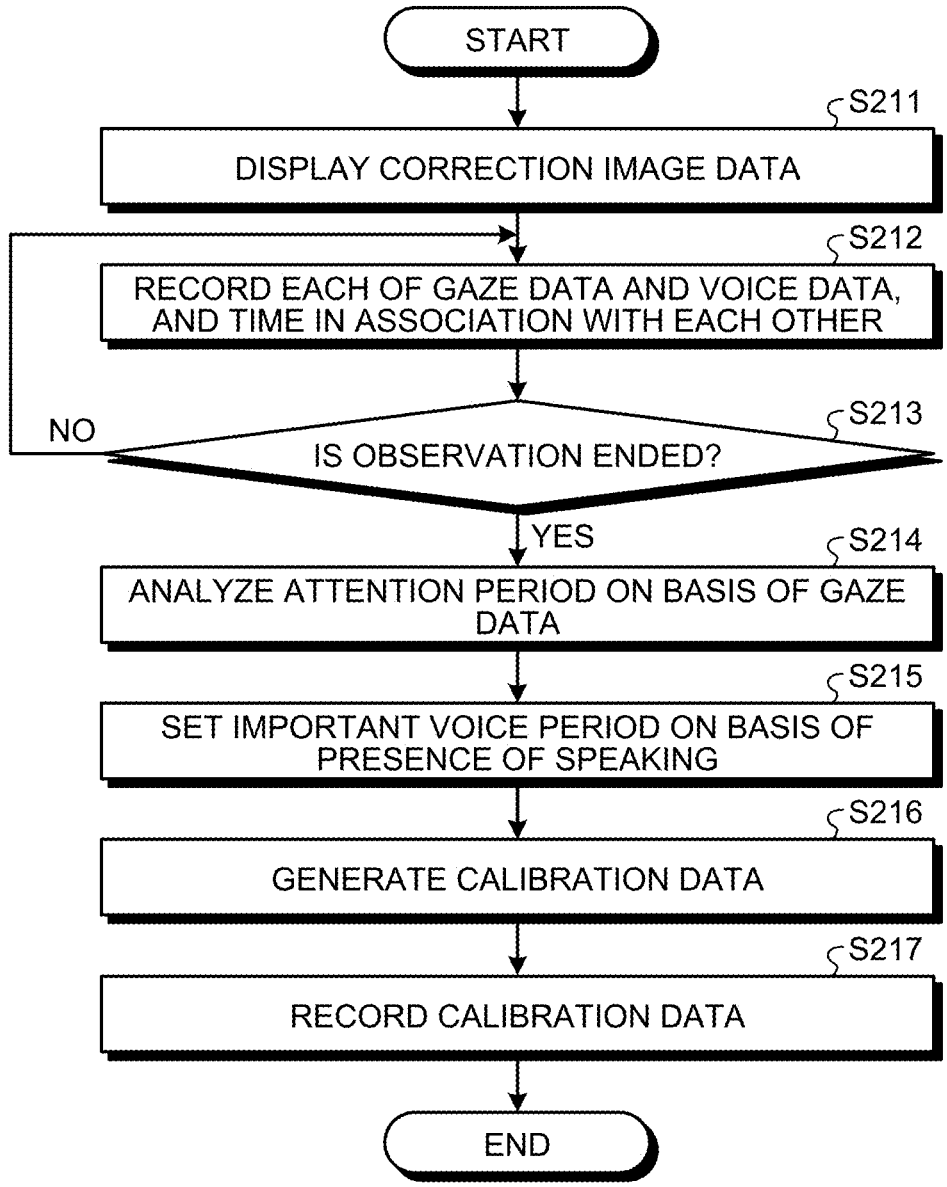

FIG.19B

| INDEX | GAZE DATA | | VOICE DATA | |
|---|---|---|---|---|
| | START TIME | END TIME | START TIME | END TIME |
| 1 | 0:10 | 0:15 | 0:11 | 0:17 |
| 2 | 0:28 | 0:38 | 0:30 | 0:42 |
| ... | ... | ... | ... | ... |
| 10 | 3:56 | 4:10 | 3:56 | 4:08 |
| ... | ... | ... | ... | ... |

INFORMATION PROCESSING APPARATUS, INFORMATION PROCESSING METHOD, AND NON-TRANSITORY COMPUTER READABLE RECORDING MEDIUM

CROSS-REFERENCE TO RELATED APPLICATION

This application is based upon and claims the benefit of priority from Japanese Patent Application No. 2018-095520, filed on May 17, 2018 and Japanese Patent Application No. 2019-090107, filed on May 10, 2019, the entire contents of which are incorporated herein by reference.

BACKGROUND

The present disclosure relates to an information processing apparatus that processes voice data and gaze data, an information processing method, and a non-transitory computer readable recording medium.

Recently, in an information processing apparatus that processes information such as image data, a technology is known in which in a period tracing back to a predetermined time from a time when a voice of a user is detected, a display area of an image at which a gaze of the user stays for the longest period is detected as attention information with respect to a plurality of display areas on an image that is displayed on a display unit, and the attention information and the voice are recorded by being associated with each other (refer to Japanese Patent Publication No. 4282343).

In addition, in a gazing annotation system, a technology is known in which an annotation anchor is displayed close to a attention point at which a user gazes, detected by a gazing tracking device, with respect to an image that is displayed on a display device of a computing device, and information is input into the annotation anchor by a voice (refer to Japanese Patent Application Laid-open Publication No. 2016-181245).

SUMMARY

According to a first aspect of the present disclosure, an information processing apparatus is provided which includes a display that displays a correction image in which a coordinate position of each of a plurality of observation points is set; a first memory that records correction voice data in which a voice to be pronounced at each of the plurality of observation points of the correction image is set; a gaze detector that generates gaze data by continuously detecting a gaze of a user; a voice input device that generates voice data associated with a time axis identical to that of the gaze data by receiving input of a voice of the user; and a hardware processor configured to, analyze a attention period in which a attention degree of the gaze of the user with respect to each of the plurality of observation points is greater than or equal to a predetermined value, on the basis of the gaze data that is generated by the gaze detector, set a period in which the voice is pronounced with respect to the voice data as an important voice period, on the basis of the correction voice data that is recorded in the first memory, and generate calibration data of the user on the basis of a time lag between the attention period and the important voice period to be recorded in a second memory.

According to a second aspect of the present disclosure, an information processing method is provided which includes displaying a correction image in which a coordinate position of each of a plurality of observation points is set; generating gaze data by continuously detecting a gaze of a user; generating voice data associated with a time axis identical to that of the gaze data by receiving input of a voice of the user; analyzing a attention period in which a attention degree of the gaze of the user with respect to each of the plurality of observation points is greater than or equal to a predetermined value, on the basis of the generated gaze data; setting a time when the voice is pronounced with respect to the voice data as an important voice period, on the basis of correction voice data recorded in a first memory that records the correction voice data in which a voice to be pronounced at each of the plurality of observation points of the correction image is set; and generating a time lag between the attention period and the important voice period as calibration data of the user to be recorded in a second memory.

According to a third aspect of the present disclosure, a non-transitory computer readable recording medium is provided which records a program of allowing an information processing apparatus to execute: displaying a correction image in which a coordinate position of each of a plurality of observation points is set; generating gaze data by continuously detecting a gaze of a user; generating voice data associated with a time axis identical to that of the gaze data by receiving input of a voice of the user; analyzing a attention period in which a attention degree of the gaze of the user with respect to each of the plurality of observation points is greater than or equal to a predetermined value, on the basis of the generated gaze data; setting a time when the voice is pronounced with respect to the voice data as an important voice period, on the basis of correction voice data recorded in a first memory that records the correction voice data in which a voice to be pronounced at each of the plurality of observation points of the correction image is set; and generating a time lag between the attention period and the important voice period as calibration data of the user to be recorded in a second memory.

BRIEF DESCRIPTION OF THE DRAWINGS

FIG. 2 is a flowchart illustrating an outline of processing that is executed by the information processing apparatus according to the first embodiment of the present disclosure;

FIG. 3 is a diagram schematically illustrating an analysis method of an attention period in which an attention degree of a gaze with an analysis unit according to the first embodiment of the present disclosure is greater than or equal to a predetermined value;

FIG. 4 is a diagram schematically illustrating a setting method of an important voice period of voice data with a setting unit according to the first embodiment of the present disclosure;

FIG. 6B is a flowchart illustrating an outline of processing that is executed by the information processing apparatus according to the second embodiment of the present disclosure;

FIG. 7B is a flowchart illustrating an outline of processing that is executed by the information processing apparatus according to the modification example of the second embodiment of the present disclosure;

FIG. 19B is a diagram illustrating an example of data in which gaze data and voice data are associated with each other, according to a modification example of the fourth embodiment of the present disclosure;

DETAILED DESCRIPTION

Hereinafter, modes for carrying out the present disclosure will be described in detail along with the drawings. Furthermore, the present disclosure is not limited by the following embodiments. In addition, each of the drawings referred to by the following description merely schematically illustrates a shape, a size, and a position relationship to the extent that the contents of the present disclosure can be understood. That is, the present disclosure is not limited to the shape, the size, and the position relationship exemplified in each of the drawings.

First Embodiment

Configuration of Information Processing Apparatus

Figure 1:
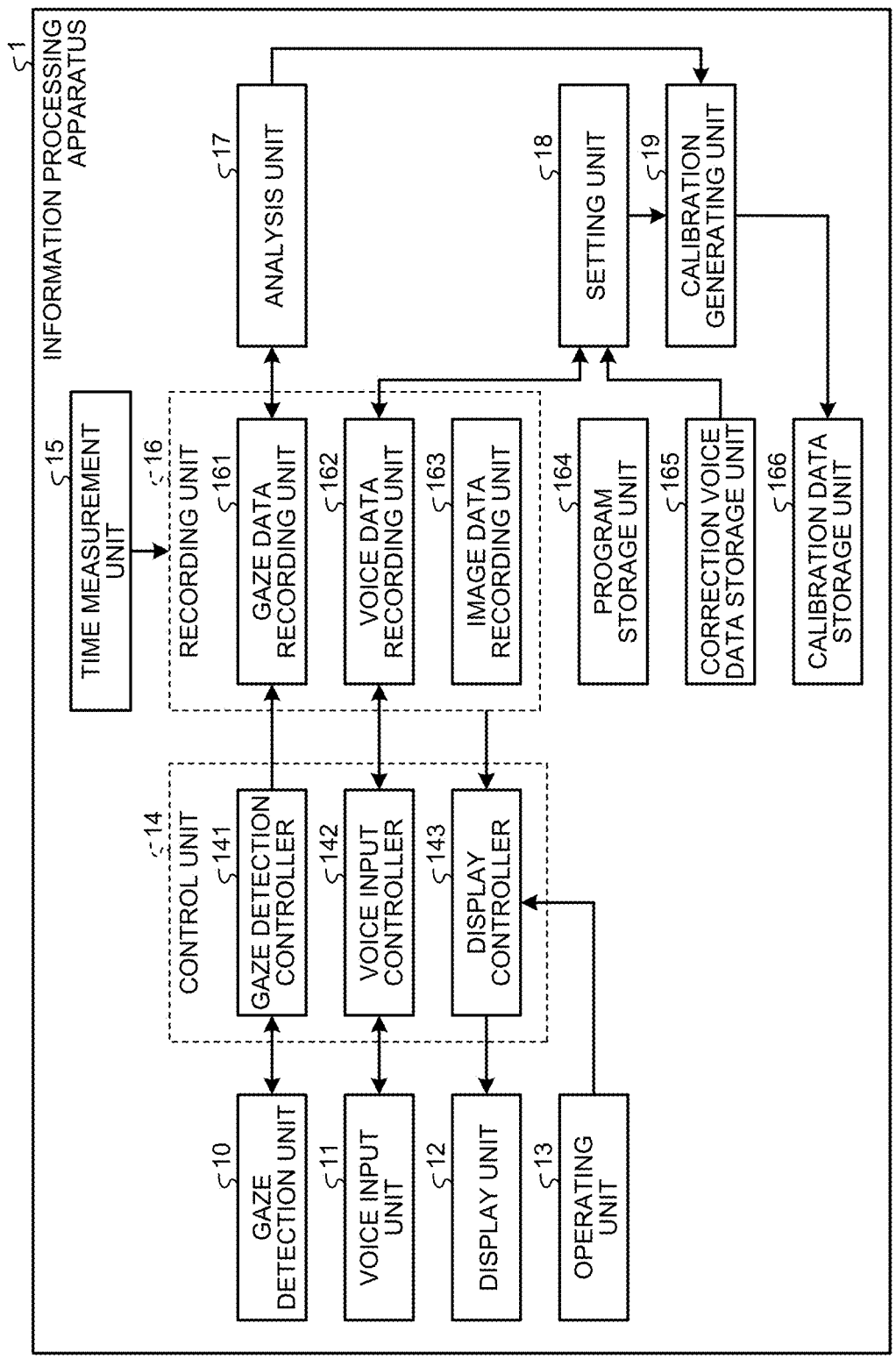
FIG. 1 is a block diagram illustrating a functional configuration of an information processing apparatus according to a first embodiment of the present disclosure.

FIG. 1 is a block diagram illustrating a functional configuration of an information processing apparatus according to a first embodiment. An information processing apparatus 1 illustrated in FIG. 1 includes a gaze detection unit 10, a voice input unit 11, a display unit 12, an operating unit 13, a control unit 14, a time measurement unit 15, a recording unit 16, an analysis unit 17, a setting unit 18, a calibration generating unit 19, a program storage unit 164, a correction voice data storage unit 165, and a calibration data storage unit 166.

The gaze detection unit 10 is configured by using an LED light source that emits a near infrared ray, and an optical sensor (for example, a CMOS, a CCD, or the like) that captures a pupil point and a reflex point on a cornea. The gaze detection unit 10 generates gaze data by detecting a gaze of a user with respect to a correction image that is displayed on the display unit 12, and outputs the gaze data to the control unit 14, under the control of the control unit 14. Specifically, the gaze detection unit 10 generates the gaze data by irradiating the cornea of the user with a near infrared ray from the LED light source or the like, and by allowing the optical sensor to capture the pupil point and the reflex point on the cornea of the user, under the control of the control unit 14. Then, the gaze detection unit 10 generates gaze data of a predetermined time by continuously calculating the gaze of the user or a gaze from a pattern of the pupil point and the reflex point of the user, on the basis of an analysis result analyzed by performing image processing or the like with respect to data that is generated by the optical sensor, and outputs the gaze data to a gaze detection controller 141 described below, under the control of the control unit 14. Furthermore, the gaze detection unit 10 may generate the gaze data in which the gaze of the user is detected by simply detecting the pupil of the user only with the optical sensor by using known pattern matching, or may generate the gaze data by detecting the gaze of the user by using other sensors or other known technologies.

The voice input unit 11 is configured by using a microphone to which a voice is input, and a voice codec that converts the voice of which the input is received by the microphone into digital voice data, and outputs the voice data to the control unit 14 by amplifying the voice data. The voice input unit 11 generates the voice data by receiving the input of the voice of the user, and outputs the voice data to the control unit 14, under the control of the control unit 14. Furthermore, the voice input unit 11 may be provided with a voice output function by including a speaker or the like that is capable of outputting a voice, in addition to the input of the voice.

The display unit 12 displays the correction image in which a coordinate position of each of a plurality of observation points is set, under the control of the control unit 14. The display unit 12 is configured by using a display panel such as a liquid crystal display panel or an organic electro luminescence (EL) display panel, and the like.

The operating unit 13 receives the input of various operations relevant to the information processing apparatus 1. The operating unit 13, for example, is configured by using a switch, a touch panel, a keyboard, a mouse, and the like.

The control unit 14 is configured by using a central processing unit (CPU), a field programmable gate array (FPGA), a graphics processing unit (GPU), and the like, and controls the gaze detection unit 10, the voice input unit 11, and the display unit 12. The control unit 14 includes the gaze detection controller 141, a voice input controller 142, and a display controller 143.

The gaze detection controller 141 controls the gaze detection unit 10. Specifically, the gaze detection controller 141 allows the gaze detection unit 10 to generate the gaze data by irradiating a user U1 with a near infrared ray at each predetermined timing, and by capturing the pupil of the user U1. In addition, the gaze detection controller 141 performs various pieces of image processing with respect to the gaze data that is input from the gaze detection unit 10, and outputs the gaze data to the recording unit 16.

The voice input controller 142 controls the voice input unit 11, performs various pieces of processing, for example, gain-up processing, noise reduction processing, or the like with respect to the voice data that is input from the voice input unit 11, and outputs the voice data to the recording unit 16.

The display controller 143 controls a display mode of the display unit 12. The display controller 143 allows the display unit 12 to display an image corresponding to image data that is recorded in the recording unit 16 or a visualized image corresponding to data to which gaze data or voice data is converted.

The time measurement unit 15 is configured by using a timer, a clock generator, or the like, and applies time information to the gaze data that is generated by the gaze detection unit 10, the voice data that is generated by the voice input unit 11, and the like.

The recording unit 16 is configured by using a volatile memory, a non-volatile memory, a recording medium, and the like, and records various information items relevant to an information processing apparatus 1. The recording unit 16 includes a gaze data recording unit 161, a voice data recording unit 162, and an image data recording unit 163.

The gaze data recording unit 161 records the gaze data that is input from the gaze detection controller 141, and outputs the gaze data to the analysis unit 17.

The voice data recording unit 162 records the voice data that is input from the voice input controller 142, and outputs the voice data to a setting unit 18.

The image data recording unit 163 records a plurality of image data items. Specifically, the image data recording unit 163 records correction image data in which the coordinate position of each of the plurality of observation points is set.

The program storage unit 164 stores various programs that are executed by the information processing apparatus 1, data that is used during the execution of various programs (for example, dictionary information or text conversion dictionary information), and processing data during the execution of various programs.

The correction voice data storage unit 165 stores correction voice data in which a voice to be pronounced at each of the plurality of observation points of the correction image that is displayed on the display unit 12 is set.

The calibration data storage unit 166 stores calibration data that is generated by the calibration generating unit 19 described below.

The analysis unit 17 analyzes a attention period in which a attention degree of the gaze of the user with respect to each of the plurality of observation points on the correction image that is displayed on the display unit 12 is greater than or equal to a predetermined value, on the basis of the gaze data that is recorded in the gaze data recording unit 161. Specifically, the analysis unit 17 detects any one of a moving speed of the gaze, a moving distance of the gaze within a predetermined time, and a residence time of the gaze within a prescribed area, and thus, analyzes the attention period in which the attention degree of the gaze (a attention point) is greater than or equal to a predetermined value, on the basis of the gaze data. The analysis unit 17, for example, is configured by using a CPU, an FPGA, a GPU, and the like.

The setting unit 18 sets a period (a time) in which the voice to be pronounced at each of the plurality of observation points of the correction image with respect to the voice data that is recorded in the voice data recording unit 162 is pronounced, as an important voice period, on the basis of the correction voice data that is recorded in the correction voice data storage unit 165. The setting unit 18 is configured by using a CPU, an FPGA, a GPU, and the like.

The calibration generating unit 19 generates a time lag between the attention period that is analyzed by the analysis unit 17 and the important voice period that is set by the setting unit 18, as the calibration data of the user to be recorded in the calibration data storage unit 166 of the recording unit 16. The calibration data relates to a time lag based on a start time or an end time of any one of the gaze data and the voice data, or the length of a period based on any one of the gaze data and the voice data. Furthermore, the calibration generating unit 19 calculates the time lag between the attention period and the important voice period multiple times, and generates calibration data on the basis of statistical characteristics of a plurality of calculation results. In addition, the calibration generating unit 19 may generate a time lag between a start time of the attention period and a start time of the important voice period, or a time lag between an end time of the attention period and an end time of the voice important period, as the calibration data. For example, even though it is not illustrated, the user or an emendator prepares both of the display of the correction image and an important word. Specifically, in a case of an image of a microscope, the user or the emendator prepares in advance an image that is known as having a predetermined lesion, and prepares a term (a keyword) that relates to the legion, as the important word. The calibration generating unit 19 measures a time lag from a time when the user focuses on the legion to a time when a predetermined important word is uttered, as the calibration data. In addition, it is desirable that the calibration generating unit 19 performs the measurement multiple times in order to increase the accuracy of the calibration data.

Processing of Information Processing Apparatus

Next, processing that is executed by the information processing apparatus 1 will be described. FIG. 2 is a flowchart illustrating the outline of the processing that is executed by the information processing apparatus 1.

As illustrated in FIG. 2, first, the display controller 143 allows the display unit 12 to display the correction image corresponding to the correction image data that is recorded in the image data recording unit 163 (Step S101).

Subsequently, the control unit 14 records each of the gaze data that is generated by the gaze detection unit 10 and the voice data that is generated by the voice input unit 11, and a time that is measured by a time measurement unit 15 in the gaze data recording unit 161 and the voice data recording unit 162 in association with each other (Step S102).

After that, in a case where an instruction signal of ending the observation of the correction image that is displayed on the display unit 12 is input from the operating unit 13 (Step S103: Yes), the information processing apparatus 1 proceeds to Step S104 described below. On the contrary, in a case where the instruction signal of ending the observation of the correction image that is displayed on the display unit 12 is not input from the operating unit 13 (Step S103: No), the information processing apparatus 1 returns to Step S102 described above.

In Step S104, the analysis unit 17 analyzes the attention period in which the attention degree of the gaze of the user with respect to each of the plurality of observation points on the correction image that is displayed on the display unit 12 is greater than or equal to a predetermined value, on the basis of the gaze data that is recorded in the gaze data recording unit 161. After Step S104, the information processing apparatus 1 proceeds to Step S105 described below.

FIG. 3 is a diagram schematically illustrating an analysis method of the attention period in which the attention degree of the gaze is greater than or equal to a predetermined value with the analysis unit 17. In (a) of FIG. 3 and (b) of FIG. 3, a horizontal axis represents a time; a vertical axis in (a) of FIG. 3 represents a moving speed; and a vertical axis in (b) of FIG. 3 represents an attention degree. In addition, a curve L1 in (a) of FIG. 3 represents a time change in the moving speed of the gaze, and a curve L2 in (b) of FIG. 3 represents a time change in the attention degree.

In general, it is possible to analyze that the attention degree of the user decreases as the moving speed of the gaze increases, and the attention degree of the gaze of the user increases as the moving speed of the gaze decreases. That is, as illustrated by the curve L1 and the curve L2 of FIG. 3, the analysis unit 17 analyzes that the attention degree of the gaze of the user decreases as the moving speed of the gaze of the user increases, and analyzes that the attention degree of the gaze of the user increases as the moving speed of the gaze decreases (refer to a attention period D1 in which the moving speed of the gaze is low). As described above, the analysis unit 17 analyzes the attention degree of the gaze of the user with respect to the gaze data at a time when the user performs observation or diagnostic interpretation with respect to the correction image, as the attention period in which the attention degree is greater than or equal to a predetermined value (for example, the attention period D1). Furthermore, in FIG. 3, the analysis unit 17 analyzes the moving speed of the gaze of the user, and thus, analyzes the attention degree of the gaze of the user, but is not limited thereto, and may analyze the attention degree of the gaze by detecting any one of the moving distance of the gaze of the user within the predetermined time and the residence time of the gaze of the user within the prescribed area.

Returning to FIG. 2, Step S105 and the subsequence will be continuously described.

In Step S105, the setting unit 18 sets the time when the voice to be pronounced at each of the plurality of observation points of the correction image with respect to the voice data that is recorded in the voice data recording unit 162 is pronounced, as the important voice period, on the basis of the correction voice data that is recorded in the correction voice data storage unit 165. After Step S105, the information processing apparatus 1 proceeds to Step S106 described below.

FIG. 4 is a diagram schematically illustrating a setting method of the important voice period of the voice data with the setting unit 18. In FIG. 4, a horizontal axis represents a time, a vertical axis in (a) of FIG. 4 represents voice data (phonation), and a vertical axis in (b) of FIG. 4 represents a voice importance degree. In addition, a curve L3 in (a) of FIG. 4 represents a time change in the voice data, and a curve L4 in (b) of FIG. 4 represents a time change in the voice importance degree of the voice data.

As illustrated by the curve L3 and curve L4 of FIG. 4, the setting unit 18 sets the period (the time) in which the voice to be pronounced at each of the plurality of observation points of the correction image with respect to the voice data that is recorded in the voice data recording unit 162 is pronounced, as the important voice period, on the basis of the correction voice data that is recorded in the correction voice data storage unit 165. For example, in a case where there is "cancer" in the correction voice data that is recorded in the correction voice data storage unit 165, the setting unit 18 sets a time when the user pronounces "cancer" (a voice important section D2) as the important voice period.

Returning to FIG. 2, Step S106 and the subsequence will be continuously described.

In Step S106, the calibration generating unit 19 generates the calibration data. After Step S106, the information processing apparatus 1 proceeds to Step S107 described below.

Figure 5A:
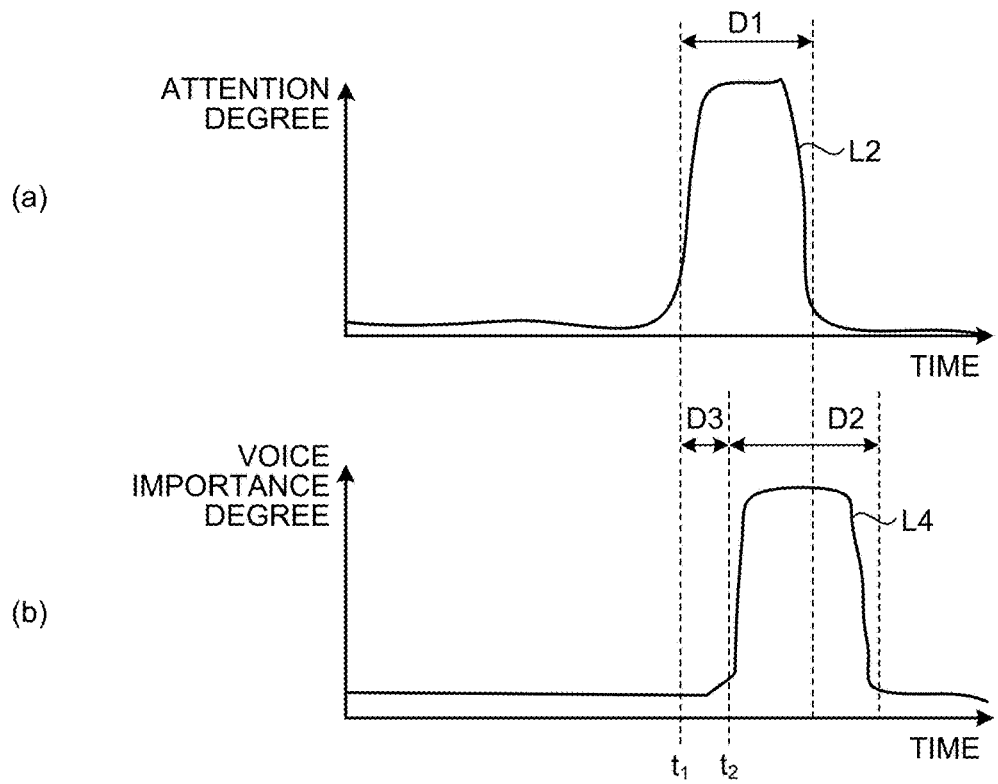
FIG. 5A is a diagram schematically illustrating a generating method of calibration data with a calibration generating unit according to the first embodiment of the present disclosure.

FIG. 5A is a diagram schematically illustrating a generating method of the calibration data with the calibration generating unit 19. In FIG. 5A, a horizontal axis represents a time, a vertical axis in (a) of FIG. 5A represents an attention degree, and a vertical axis in (b) of FIG. 5A represents a voice importance degree. In addition, a curve L2 in (a) of FIG. 5A (or the curve L2 in (b) of FIG. 3) represents a time change in the attention degree; and a curve L4 in (b) of FIG. 5A (or the curve L4 in (b) of FIG. 4) represents a time change in the voice importance degree.

As illustrated by the curve L2 and the curve L4 of FIG. 5A, the calibration generating unit 19 generates a time lag D3 between a start time $t_1$ of the attention period D1 that is analyzed by the analysis unit 17 and a start time $t_2$ of the important voice period D2 that is set by the setting unit 18, as the calibration data of the user.

Figure 5B:
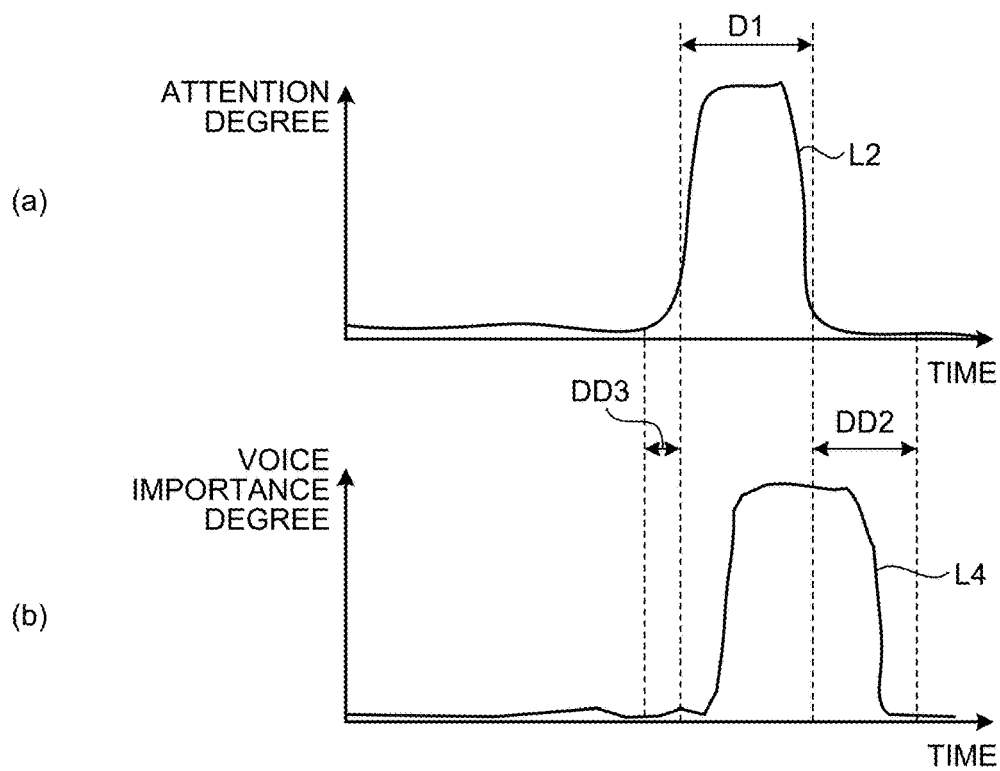
FIG. 5B is a diagram schematically illustrating another generating method of the calibration data with the calibration generating unit according to the first embodiment of the present disclosure.

In addition, as a modification example, in a case where a timing of a period in which the attention degree of the user is high and a period in which the important word is spoken varies for each measurement, such a variation period may be considered. That is, as illustrated in FIG. 5B, the calibration generating unit 19 adjusts margins DD2 and DD3 before and after a time frame is set, according to the size of the variation, and sets the calibration data having a large margin as the variation increases.

Returning to FIG. 2, Step S107 and the subsequence will be continuously described.

In Step S107, the calibration generating unit 19 records the calibration data that is generated in Step S106, in the calibration data storage unit 166. After Step S107, the information processing apparatus 1 ends this processing.

According to the first embodiment described above, the calibration generating unit 19 generates the time lag D3 between the attention period D1 that is analyzed by the analysis unit 17 and the important voice period D2 that is set by the setting unit 18, as the calibration data of the user, and thus, it is possible to correct the time lag between the attention point of the gaze and the time when the voice is output.

In addition, according to the first embodiment, the calibration generating unit 19 generates the time lag D3 between the start time $t_1$ of the attention period D1 that is analyzed by the analysis unit 17 and the start time $t_2$ of the important voice period D2 that is set by the setting unit 18, as the calibration data of the user, and thus, it is possible to more accurately correct the time lag between the attention point of the gaze and the time when the voice is output.

Furthermore, in the first embodiment, the calibration generating unit 19 may calculate each time lag between a plurality of attention periods and a plurality of important voice periods multiple times, and may generate the calibration data on the basis of statistical characteristics of a plurality of calculation results. Accordingly, it is possible to more accurately correct the time lag between the attention point of the gaze and the time when the voice is output.

Second Embodiment

Next, a second embodiment of the present disclosure will be described. In the first embodiment described above, the setting unit 18 sets the important voice period of the voice data, on the basis of the correction voice data, but in the second embodiment, a period in which a keyword designated in advance is pronounced according to an operation signal that is input from the operating unit 13 is set as the important voice period of the voice data. Hereinafter, the configuration of an information processing apparatus according to the second embodiment will be described, and then, processing that is executed by the information processing apparatus according to the second embodiment will be described. Furthermore, the same reference numerals will be applied to the same configurations as those of the information processing apparatus 1 according to the first embodiment described above, and the detailed description thereof will be omitted.

Configuration of Information Processing Apparatus

Figure 6A:
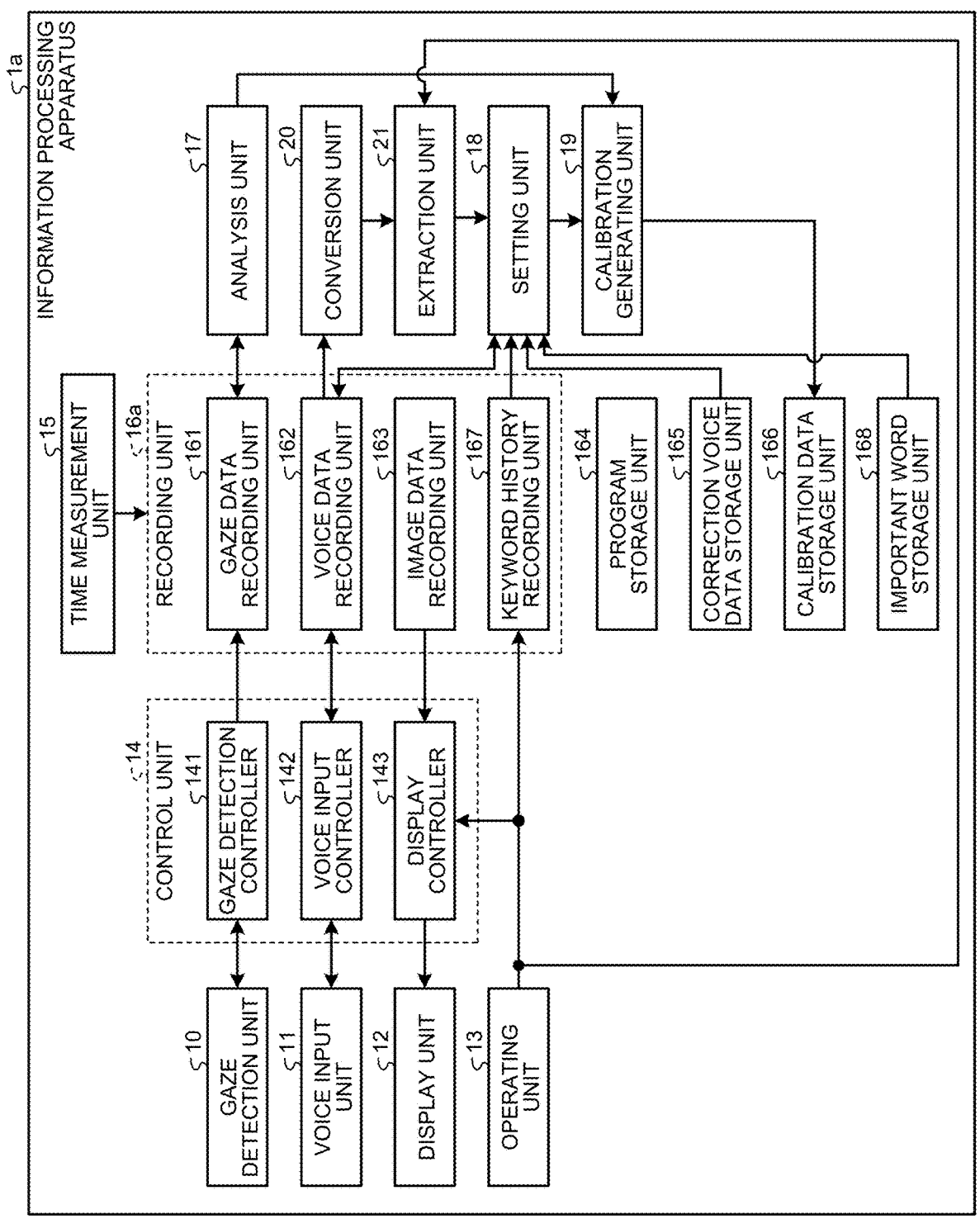
FIG. 6A is a block diagram illustrating a functional configuration of an information processing apparatus according to a second embodiment of the present disclosure.

FIG. 6A is a block diagram illustrating a functional configuration of the information processing apparatus according to the second embodiment. An information processing apparatus 1a illustrated in FIG. 6A includes a recording unit 16a instead of the recording unit 16 of the information processing apparatus 1 according to the first embodiment described above. Further, the information processing apparatus 1a includes a conversion unit 20, an extraction unit 21, and an important word storage unit 168.

The recording unit 16a includes a keyword history recording unit 167 recording a plurality of keywords that are input from the operating unit 13 in the past, in addition to the configuration of the recording unit 16 according to the first embodiment described above. Here, the plurality of keywords that are input in the past, for example, are extracted keywords that are set by analyzing the frequency of a word input in the past through the operating unit 13.

The conversion unit 20 performs known text conversion processing with respect to the voice data, and thus, converts the voice data into character information (text data), and outputs the character information to the extraction unit 21. Furthermore, the character conversion of the voice may not be performed at this time point, and at this time, the importance degree may be set as voice information, and then, may be converted into the character information.

The extraction unit 21 extracts a keyword corresponding to the instruction signal that is input from the operating unit 13, a keyword that is recorded in the keyword history recording unit 167, and a keyword that is recorded in the important word storage unit 168, from the character information that is converted by the conversion unit 20, and outputs an extraction result to the setting unit 18.

The important word storage unit 168 stores a plurality of keywords that are an important word set in advance. Here, the important word set in advance is a word (a keyword) that is set by a manufacturer or the like before the information processing apparatus 1a is shipped or through a network (not illustrated).

Processing of Information Processing Apparatus

Next, processing that is executed by the information processing apparatus 1a will be described. FIG. 6B is a flowchart illustrating the outline of the processing that is executed by the information processing apparatus 1a. In FIG. 6B, Step S201 and Step S202 respectively correspond to Step S101 and Step S102 of FIG. 2 described above.

In Step S203, the conversion unit 20 converts voice data that is recorded in a voice data recording unit 162 into character information. After Step S203, the information processing apparatus 1a proceeds to Step S204 described below. Step S204 and Step S205 respectively correspond to Step S103 and Step S104 of FIG. 2 described above. After Step S205, the information processing apparatus 1a proceeds to Step S206.

Subsequently, the extraction unit 21 extracts a pronunciation time when the keyword that is recorded in the keyword history recording unit 167 or the keyword that is recorded in the important word storage unit 168 appears, from the character information that is converted by the conversion unit 20 (Step S206).

After that, the setting unit 18 sets the time when the voice to be pronounced at each of the plurality of observation points of the correction image with respect to the voice data that is recorded in the voice data recording unit 162 is pronounced, as the important voice period, on the basis of a pronunciation time that is extracted by the extraction unit 21 (Step S207).

Step S208 and Step S209 respectively correspond to Step S106 and Step S107 of FIG. 2 described above. After Step S209, the information processing apparatus 1a ends this processing.

According to the second embodiment described above, the calibration generating unit 19 generates the time lag between the start time of the attention period that is analyzed by the analysis unit 17 and the start time of the important voice period that is set by the setting unit 18, as the calibration data of the user, and thus, it is possible to correct the time lag between the attention point of the gaze and the time when the voice is output. Furthermore, as with the first embodiment, in a case where a variation occurs in a plurality of measurements, such a variation is considered in the calibration data.

Modification Example of Second Embodiment

Next, a modification example of the embodiment of the present disclosure will be described. In the first embodiment described above, the setting unit 18 sets the important voice period of the voice data, on the basis of the correction voice data, but in the modification example of the second embodiment, a setting unit sets a period in which a voice is output, as the important voice period without converting the voice data into the character information. Hereinafter, the configuration of an information processing apparatus according to the modification example of the embodiment will be described, and then, processing that is executed by the information processing apparatus according to the modification example of the second embodiment will be described. Furthermore, the same reference numerals will be applied to the same configurations as those of the information processing apparatus 1 according to the first embodiment described above, and the detailed description thereof will be omitted.

Configuration of Information Processing Apparatus

Figure 7A:
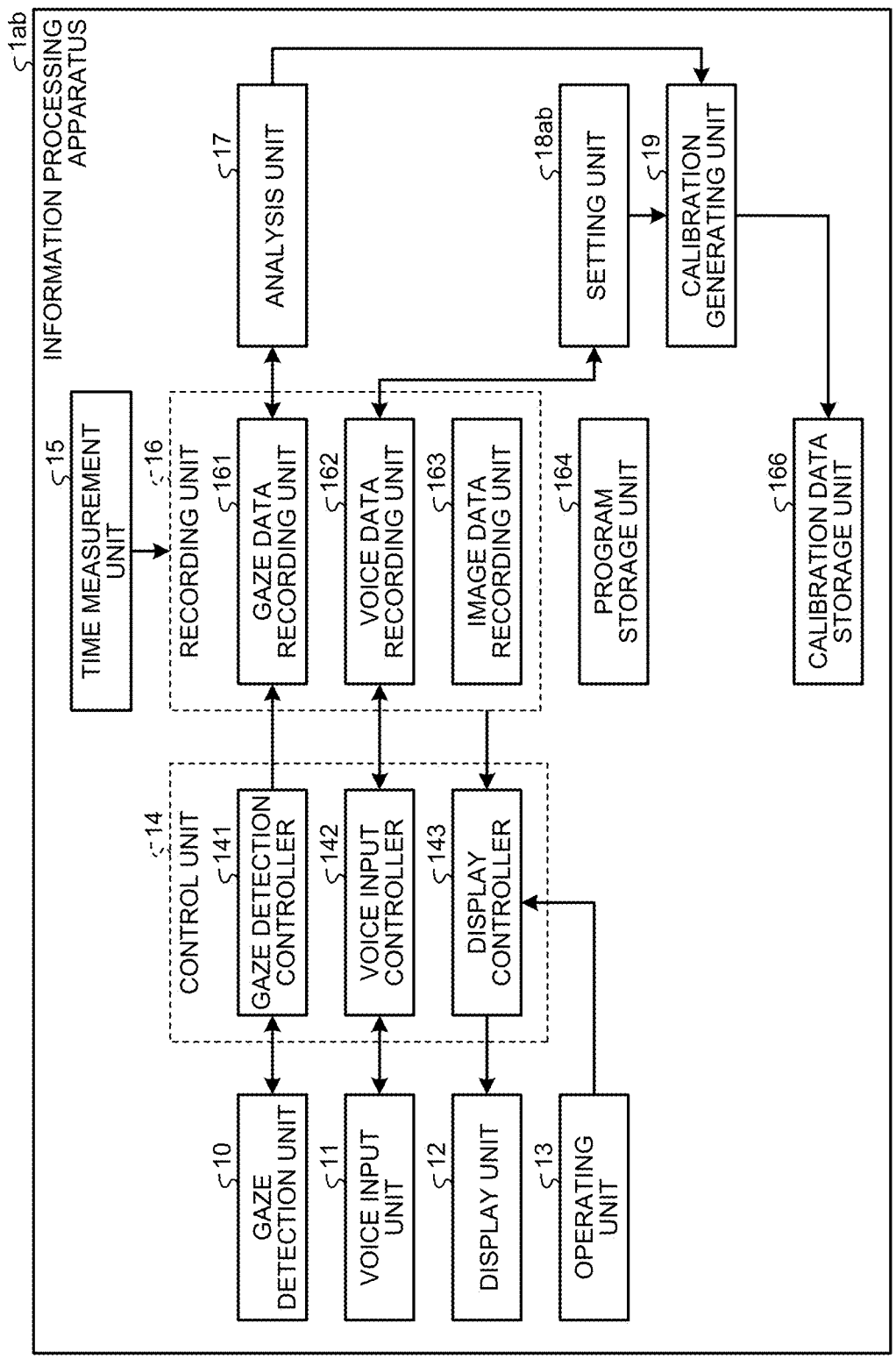
FIG. 7A is a block diagram illustrating a functional configuration of an information processing apparatus according to a modification example of the second embodiment of the present disclosure.

FIG. 7A is a block diagram illustrating a functional configuration of the information processing apparatus according to the modification example of the second embodiment. An information processing apparatus lab illustrated in FIG. 7A is configured by deleting the correction voice data storage unit 165 from the information processing apparatus 1 according to the first embodiment described above. In addition, a setting unit 18ab is different from the setting unit 18 of the information processing apparatus 1 according to the first embodiment, and sets an important voice period in which speaking is performed regardless of the contents of the voice in the voice data that is output from the voice data recording unit 162, for example, a period that is recognized that a level indicating a voice volume is greater than a constant value in a predetermined period, as the important voice period.

Processing of Information Processing Apparatus

Next, processing that is executed by the information processing apparatus lab will be described. FIG. 7B is a flowchart illustrating the outline of the processing that is executed by the information processing apparatus lab. In FIG. 7B, Step S211, Step S212, Step S213, and Step S214 respectively correspond to Step S101, Step S102, Step S103, and Step S104 of FIG. 2 described above.

In Step S215, the setting unit 18ab sets the time when the voice to be pronounced at each of the plurality of observation points of the correction image with respect to the voice data that is recorded in the voice data recording unit 162 regardless of the contents is pronounced, as the important voice period, on the basis of presence of speaking. After Step S215, the information processing apparatus lab proceeds to Step S216 described below.

Step S216 and Step S217 respectively correspond to Step S106 and Step S107 of FIG. 2 described above. After Step S217, an information processing apparatus 1aa ends this processing.

Here, the important voice period is defined by a period in which a voice is output at a time close to the attention period (the attention period and a predetermined period before and after the attention period) regardless of the contents of the words to be output. Specifically, in a case where there are a plurality of voice periods within the time close to the attention period, for example, the setting unit 18ab sets one or more of a period in which a voice having the loudest voice is output and a period in which a voice having a minimum time lag with respect to the middle of the attention period is output, as the important voice period.

In addition, the time lag between the attention period and the important voice period that is the basis of the calibration data is not limited to only at least one of the start time of the attention period and the start time of the important voice period, and the end time of the attention period and the end time of the important voice period, in FIG. 5A and FIG. 5B described above. Specifically, the time lag between the attention period and the important voice period that is the basis of the calibration data is a difference between a time corresponding to the middle of the attention period and a time corresponding to the middle of the important voice period, or a difference between a time corresponding to the center of integration of the attention period calculated by integrating with an attention degree of the attention period and the time, and a time corresponding to the center of integration of the important voice period that is calculated by integrating with the loudness of the voice and the time.

In addition, the calibration generating unit 19 may generate the calibration data by integrating the time lags that are calculated from the plurality of attention periods and the plurality of important voice periods. The calibration generating unit 19, for example, may generate unique calibration data from the average of the plurality of time lags, or may generate the calibration data as a "time range" including a variation of a predetermined factor of standard deviation from the average, on the basis of statistical information of a plurality of time lags. Further, the calibration generating unit 19 may calculate the statistical information by multiplying the corresponding attention period and weight according to the size of the area of the important voice period, and may generate the calibration data.

According to the modification example of the second embodiment described above, the calibration generating unit 19 generates the calibration data of the user on the basis of the time lag between the attention period that is analyzed by the analysis unit 17 and the important voice period that is set by the setting unit 18ab, and thus, it is possible to correct the time lag between the attention point of the gaze and the time when the voice is output.

Third Embodiment

Next, a third embodiment of the present disclosure will be described. In the first embodiment and the second embodiment described above, the calibration data with respect to the user is generated, but in the third embodiment, the time lag between the gaze of the user and the pronunciation is corrected by using the calibration data that is generated in the first embodiment and the second embodiment described above. Furthermore, the same reference numerals will be applied to the same configurations as those of the information processing apparatus 1 according to the first embodiment described above, and the detailed description thereof will be omitted.

Configuration of Information Processing System

Figure 8:
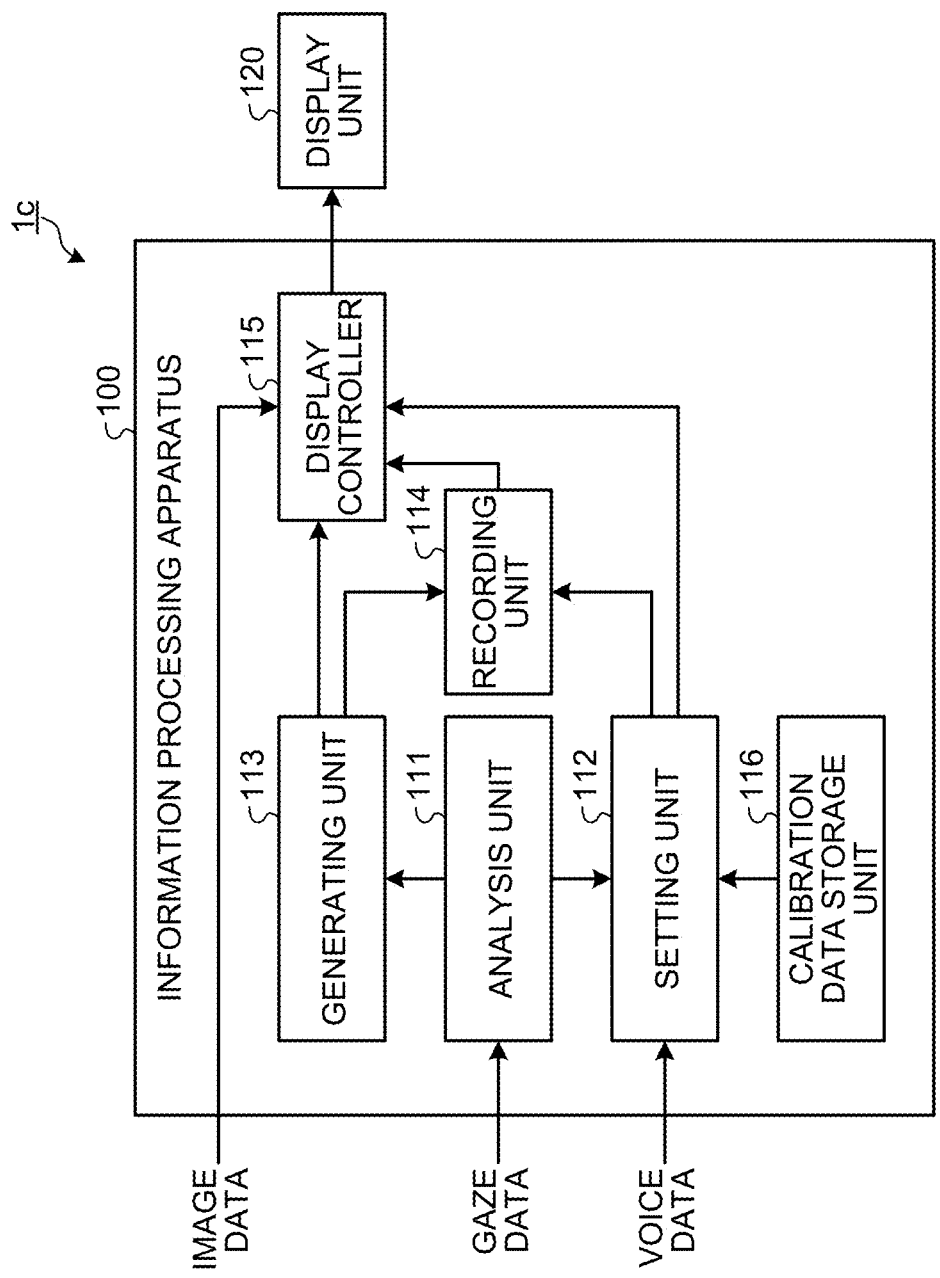
FIG. 8 is a block diagram illustrating a functional configuration of an information processing system according to a third embodiment of the present disclosure.

FIG. 8 is a block diagram illustrating a functional configuration of an information processing system according to the third embodiment. An information processing system 1c illustrated in FIG. 8 includes an information processing apparatus 100 performing various pieces of processing with respect to gaze data, voice data, and image data that are input externally, and a display unit 120 displaying various data items that are output from the information processing apparatus 100. Furthermore, the information processing apparatus 100 and the display unit 120 are bidirectionally connected in a wireless or wired manner.

Configuration of Information Processing Apparatus

First, the configuration of the information processing apparatus 100 will be described.

The information processing apparatus 100 illustrated in FIG. 8, for example, is realized by using a program that is installed in a server, a personal computer, or the like, and various data items are input into the information processing apparatus 100 through a network, or various data items that are acquired by an external device are input into the information processing apparatus 100. As illustrated in FIG. 8, the information processing apparatus 100 includes an analysis unit 111, a setting unit 112, a generating unit 113, a recording unit 114, a display controller 115, and a calibration data storage unit 116.

The analysis unit 111 analyzes the attention degree of the gaze of the user, on the basis of gaze data of a predetermined time (new gaze data) in which the gaze of the user that is input externally is detected. Here, the gaze data is based on a cornea reflection method. Specifically, the gaze data is data that is generated by capturing the pupil point and the reflex point on the cornea with the optical sensor that is the gaze detection unit 10 when the cornea of the user is irradiated with a near infrared ray from an LED light source or the like that is provided in the gaze detection unit 10 (eye tracking) of the first embodiment described above. Then, in the gaze data, the gaze of the user is calculated from the pattern of the pupil point and the reflex point of the user based on an analysis result analyzed by performing image processing or the like with respect to the data that is generated by capturing the pupil point and the reflex point on the cornea with the optical sensor.

In addition, even though it is not illustrated, when a device including the gaze detection unit 10 (not illustrated) measures the gaze data, the corresponding image data is presented to the user, and then, the gaze data is measured. In this case, in a case where an image that is displayed to the user is fixed, that is, when absolute coordinates are not changed along with a time of a display area, the device including the gaze detection unit 10 (not illustrated) may apply a relative position relationship between a measurement area and the absolute coordinates of the image to the gaze, as a fixed value. Here, the absolute coordinates indicate coordinates described on the basis of one predetermined point of the image.

In a case where a utilization form is an endoscope system or an optical microscope, a field of view that is presented in order to detect the gaze is a field of view of the image data, and thus, the relative position relationship of the observation field of view with respect to the absolute coordinates of the image is not changed. In addition, in a case where the utilization form is the endoscope system or the optical microscope, gaze detection data, and an image recorded or presented along with the detection of the gaze are used in order to generate mapping data of the field of view at the time of being recorded as a moving image.

On the other hand, in a case where the utilization form is whole slide imaging (WSI), the user observes a part of a slide sample of a microscope, as the field of view, and an observation field of view is changed along with a time. In this case, a portion of the entire image data is presented as the field of view. That is, time information of switching the absolute coordinates of the display area with respect to the entire image data is also recorded by being synchronized with the information of the gaze and the voice.

The analysis unit 111 detects any one of the moving speed of the gaze, the moving distance of the gaze within the predetermined time, and the residence time of the gaze within the prescribed area, on the basis of the gaze data of a predetermined time in which the gaze of the user that is input externally is detected, and thus, analyzes a new attention period in which the attention degree of the gaze (the attention point) is greater than or equal to a predetermined value. Furthermore, the gaze detection unit 10 (not illustrated) may detect the gaze by being provided in a predetermined location, and by capturing the user, or may detect the gaze by being provided in the user, and by capturing the user. In addition, the gaze data may be generated by known pattern matching. The analysis unit 111, for example, is configured by using a CPU, an FPGA, a GPU, and the like.

The setting unit 112 assigns an importance degree according to the attention degree that is analyzed by the analysis unit 111 and the calibration data that is recorded in a calibration data storage unit 116 with respect to the voice data of the user (new voice data) input externally associated with a time axis identical to that of the gaze data to be recorded in the recording unit 114. Specifically, the setting unit 112 corrects a time lag between a pronunciation time of the voice of the user and a attention time of the gaze for each frame of the voice data, on the basis of the calibration data, and assigns the importance degree (for example, a numerical value) according to the attention degree that is analyzed by the analysis unit 111 with respect to the corrected voice data to be recorded in the recording unit 114. In addition, the voice data of the user input externally is generated by a voice input unit such as a microphone (not illustrated) at the same timing as that of the gaze data. The setting unit 112 is configured by using a CPU, an FPGA, a GPU, and the like.

The generating unit 113 generates the gaze mapping data in which the attention degree that is analyzed by the analysis unit 111 is associated with an image corresponding to the image data that is input externally, and outputs the generated gaze mapping data to the recording unit 114 and the display controller 115. Specifically, the generating unit 113 generates the gaze mapping data in which the attention degree that is analyzed by the analysis unit 111 is associated with coordinate information on the image, in each predetermined area on the image corresponding to the image data that is input externally. Further, the generating unit 113 generates the gaze mapping data in which the locus of the gaze of the user that is analyzed by the analysis unit 111 is associated with the image corresponding to the image data that is input externally, in addition to the attention degree. The generating unit 113 is configured by using a CPU, an FPGA, a GPU, and the like. In a case of the WSI described above, when the gaze mapping data is obtained as the absolute coordinates of the image, the generating unit 113 uses a relative position relationship between the display and the absolute coordinates of the image at the time of measuring the gaze. In addition, as described above, in a case where the observation field of view is changed every moment, the generating unit 113 inputs a temporal change in absolute coordinates of Display Area=Field of View (for example, in which portion of the original image data the upper left side of the display image is positioned on the absolute coordinates).

The recording unit 114 records the voice data that is input from the setting unit 112, the importance degree that is assigned at each predetermined time interval, and the attention degree that is analyzed by the analysis unit 111 in association with each other. In addition, the recording unit 114 records the gaze mapping data that is input from the generating unit 113. In addition, the recording unit 114 records various programs that are executed by the information processing apparatus 100, and data items in the processing. The recording unit 114 is configured by using a volatile memory, a non-volatile memory, a recording medium, and the like.

The display controller 115 superimposes the gaze mapping data that is generated by the generating unit 113 on the image corresponding to the image data that is input externally, and outputs the gaze mapping data to the external display unit 120 to be displayed. The display controller 115 is configured by using a CPU, an FPGA, a GPU, and the like. Furthermore, the analysis unit 111, the setting unit 112, generating unit 113, and the display controller 115 described above may be configured such that each function can be exhibited by using any one of a CPU, an FPGA, and a GPU, and may be configured such that each function can be exhibited by using a combination of the CPU, the FPGA, and the GPU.

Configuration of Display Unit

Next, the configuration of the display unit 120 will be described.

The display unit 120 displays the image corresponding to the image data or gaze mapping information corresponding to the gaze mapping data input from the display controller 115. The display unit 120, for example, is configured by using a display monitor such as an organic electro luminescence (EL) monitor or a liquid crystal monitor.

Processing of Information Processing Apparatus

Figure 9:
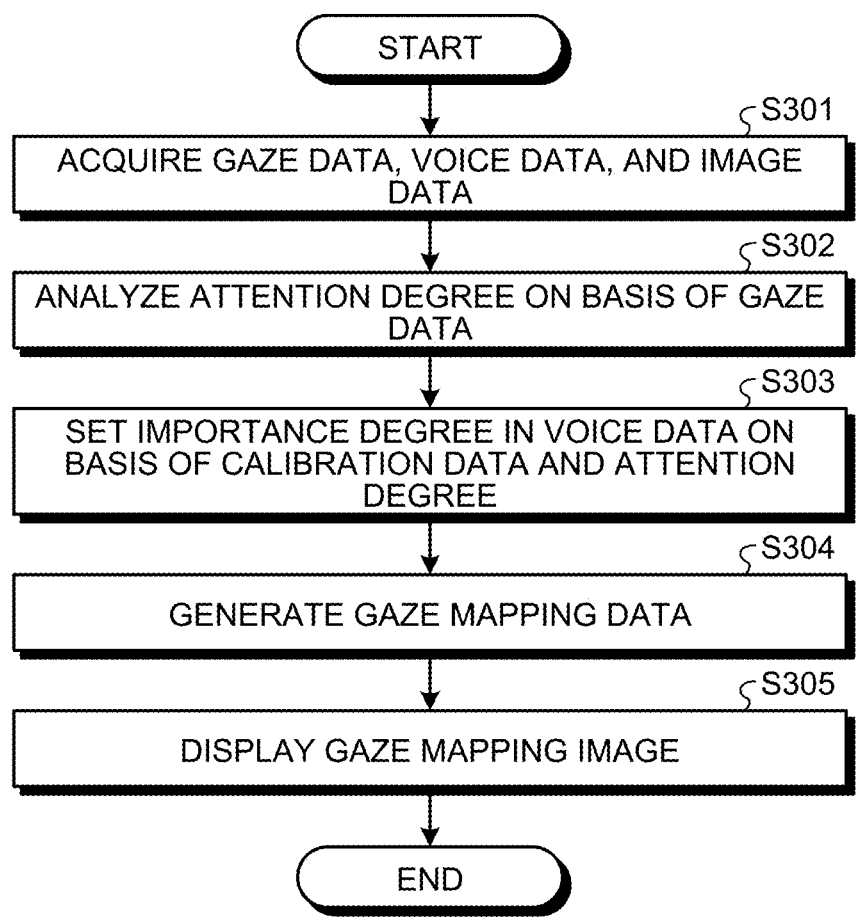
FIG. 9 is a flowchart illustrating an outline of processing that is executed by the information processing apparatus according to the third embodiment of the present disclosure.

Next, the processing of the information processing apparatus 100 will be described. FIG. 9 is a flowchart illustrating the outline of the processing that is executed by the information processing apparatus 100.

As illustrated in FIG. 9, first, the information processing apparatus 100 acquires the gaze data, the voice data, and the image data that are input externally (Step S301).

Subsequently, the analysis unit 111 analyzes the attention degree of the gaze of the user, on the basis of the gaze data (Step S302). Specifically, the analysis unit 111 analyzes the attention degree of the gaze of the user by the method described in the first embodiment of FIG. 3.

After that, the setting unit 112 performs setting of assigning the importance degree according to the calibration data that is recorded in the calibration data storage unit 116 and the attention degree that is analyzed by the analysis unit 111 with respect to the voice data that is synchronized with the gaze data to be recorded in the recording unit 114 (Step S303). Specifically, the setting unit 112 performs setting of assigning the importance degree according to the attention degree that is analyzed by the analysis unit 111 at each predetermined time interval to the voice data to be recorded in the recording unit 114, by the method described in the first embodiment of FIG. 4 and FIGS. 5A and 5B.

Subsequently, the generating unit 113 generates the gaze mapping data in which the attention degree that is analyzed by the analysis unit 111 is associated with the image corresponding to the image data (Step S304).

Subsequently, the display controller 115 superimposes the gaze mapping data that is generated by the generating unit 113 on the image corresponding to the image data, and outputs the gaze mapping data to the external display unit 120 (Step S305). After Step S305, the information processing apparatus 100 ends this processing.

Figure 10:
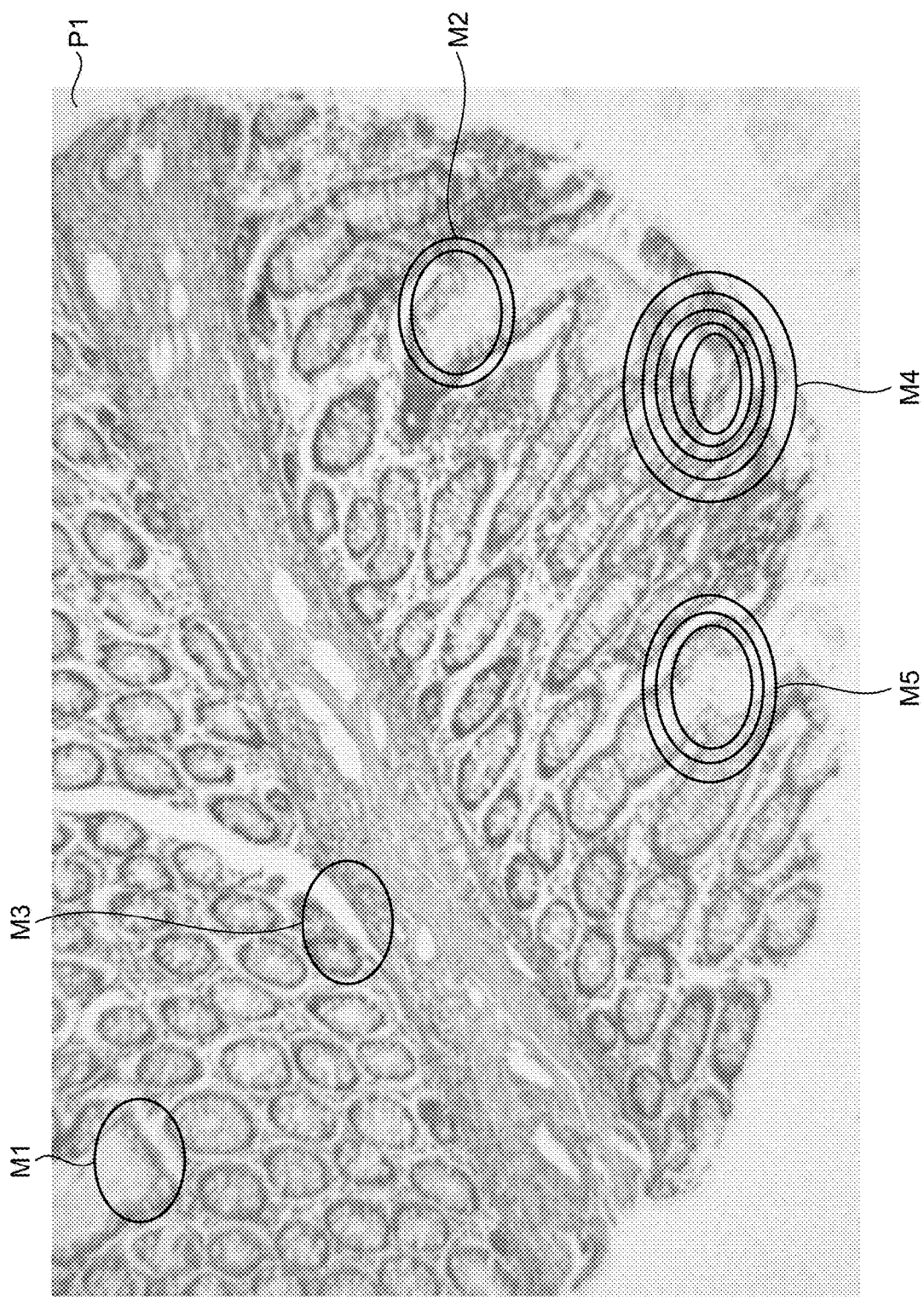
FIG. 10 is a diagram schematically illustrating an example of an image that is displayed on a display unit according to the third embodiment of the present disclosure.

FIG. 10 is a diagram schematically illustrating an example of an image that is displayed on the display unit 120. As illustrated in FIG. 10, the display controller 115 allows the display unit 120 to display a gaze mapping image P1 in which the gaze mapping data that is generated by the generating unit 113 on the image corresponding to the image data. In FIG. 10, the gaze mapping image P1 of heat maps M1 to M5 in which the number of contour lines increases as the attention degree of the gaze increases is displayed on the display unit 120.

Figure 11:
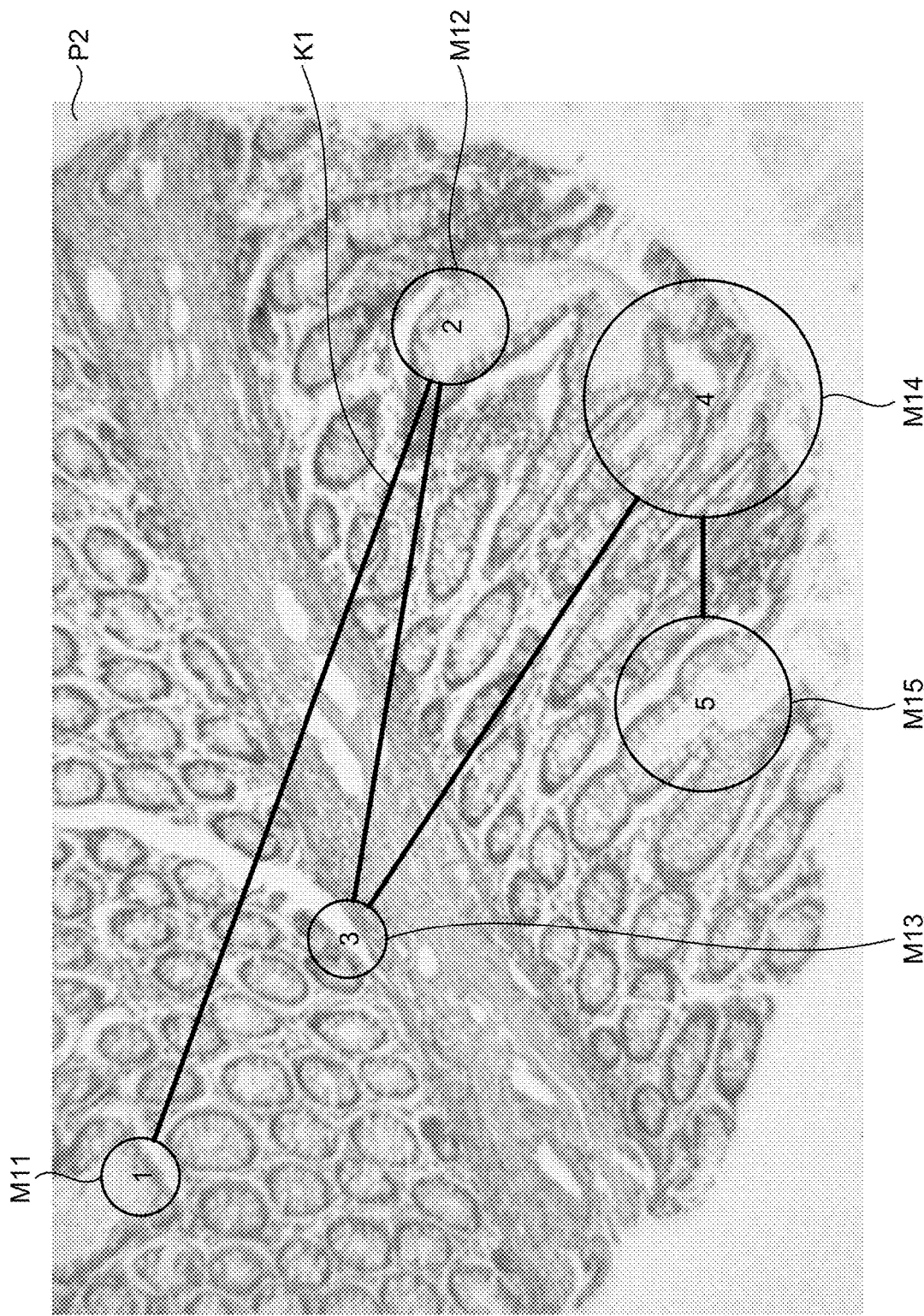
FIG. 11 is a diagram schematically illustrating another example of the image that is displayed on the display unit according to the third embodiment of the present disclosure.

FIG. 11 is a diagram schematically illustrating another example of the image that is displayed on the display unit 120. As illustrated in FIG. 11, the display controller 115 allows the display unit 120 to display the gaze mapping image P2 in which the gaze mapping data that is generated by the generating unit 113 is superimposed on the image corresponding to the image data. In FIG. 11, a gaze mapping image P2 on which marks M11 to M15 of the attention degree in which a circle area increases as the attention degree of the gaze increases are superimposed is displayed on the display unit 120. Further, the display controller 115 allows the display unit 120 to display a locus K1 of the gaze of the user and the order of the gaze in numbers. Furthermore, in FIG. 11, the display controller 115 may position the character information in which the voice data that is output by the user in the period (the time) of each of the attention degrees is converted by using a known character conversion technology in the vicinity of or to be superimposed on the marks M11 to M15, and may allow the display unit 120 to display the character information.

According to the third embodiment described above, the setting unit 112 performs the setting of assigning the importance degree according to calibration data of the user that is recorded in the calibration data storage unit 116 and the new attention degree that is newly analyzed by the analysis unit 111 with respect to the voice data (the new voice data) that is input externally to be recorded in the recording unit 114, and thus, it is possible to grasp which period of the voice data is important.

In addition, in the third embodiment, the generating unit 113 generates the attention degree that is analyzed by the analysis unit 111 and the gaze mapping data associated with the coordinate information of the attention degree, on the image corresponding to the image data that is input externally, and thus, it is possible for the user to intuitively grasp an important position on the image.

Furthermore, in the third embodiment, the setting unit 112 may set the pronunciation period in which the voice data is pronounced with respect to the voice data (the new voice data) that is input externally, and may assign the importance degree according to the new attention degree that is analyzed by the analysis unit 111 with respect to the voice data by using the pronunciation period, the new attention degree that is newly analyzed by the analysis unit 111, and the calibration data that is stored in the calibration data storage unit 116 to be recorded in the recording unit 114. Accordingly, it is possible to grasp which period of the voice data is important.

In addition, in the third embodiment, the setting unit 112 may set a period in which a predetermined keyword in the voice data (the new voice data) that is input externally is pronounced as a new important pronunciation period, and may assign the importance degree according to the new important pronunciation period with respect to the gaze data (the new gaze data) that is input externally by using the new important pronunciation period and the calibration data that is stored in the calibration data storage unit 116 to be recorded in the recording unit 114. It is possible to grasp which period of the gaze data is important.

In addition, in the third embodiment, the setting unit 112 may set the period in which the predetermined keyword in the voice data (the new voice data) that is input externally is pronounced as the new important pronunciation period, and may assign the importance degree according to the important pronunciation period with respect to the gaze data (the new gaze data) that is input externally, by using the new attention period, the new important pronunciation period, and the calibration data that is stored in the calibration data storage unit 116 to be recorded in the recording unit 114. Accordingly, it is possible to grasp which period of the voice data is important.

In addition, in the third embodiment, the recording unit 114 records the voice data to which the importance degree is assigned by the setting unit 112, and thus, it is possible to easily acquire learning data at the time of learning a correspondence relationship between the image data and the voice based on gaze mapping that is used in machine learning such as deep learning.

Modification Example of Third Embodiment

Next, a modification example of the third embodiment of the present disclosure will be described. In the third embodiment described above, the setting unit 112 assigns the importance degree according to the attention degree that is analyzed by the analysis unit 111 to the voice data to be recorded in the recording unit 114, but in the modification example of the third embodiment, the setting unit 112 assigns the importance degree to the voice data on the basis of the gaze mapping data that is generated by the generating unit 113 to be recorded in the recording unit 114. Hereinafter, the configuration of an information processing system according to the modification example of third embodiment will be described, and then, processing that is executed by the information processing apparatus according to the modification example of third embodiment will be described. Furthermore, the same reference numerals will be applied to the same configurations as those of the information processing system 1c according to the third embodiment described above, and the detailed description thereof will be omitted.

Configuration of Information Processing System

Figure 12:
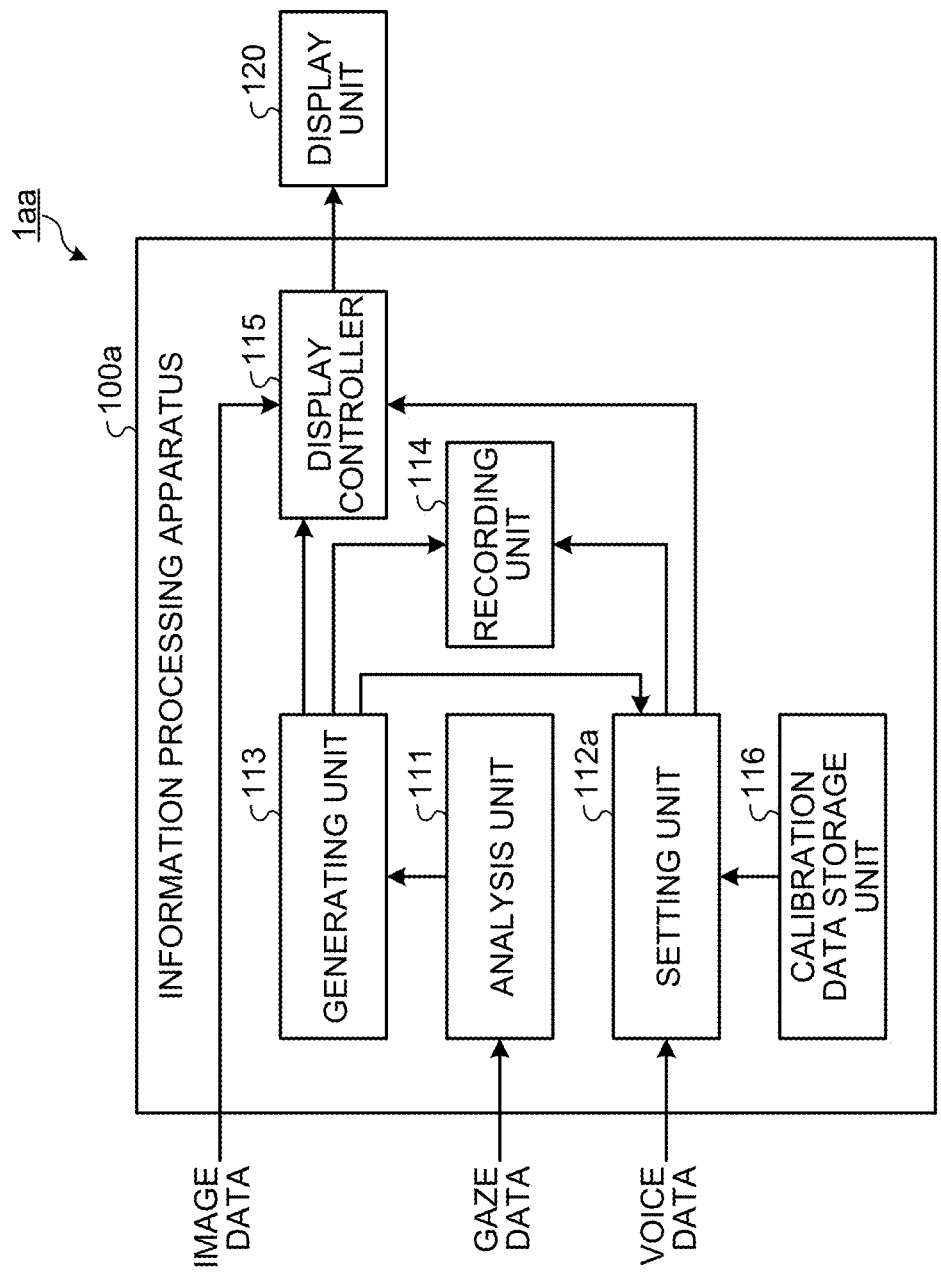
FIG. 12 is a block diagram illustrating a functional configuration of an information processing system according to a modification example of the third embodiment of the present disclosure.

FIG. 12 is a block diagram illustrating a functional configuration of the information processing system according to the modification example of the third embodiment. An information processing system 1aa illustrated in FIG. 12 includes an information processing apparatus 100a instead of the information processing apparatus 100 according to the third embodiment described above. The information processing apparatus 100a includes a setting unit 112a instead of the setting unit 112 according to the third embodiment described above.

The setting unit 112a assigns the importance degree to the voice data at each predetermined time interval on the basis of the gaze mapping data that is generated by the generating unit 113 to be recorded in the recording unit 114.

Processing of Information Processing Apparatus

Figure 13:
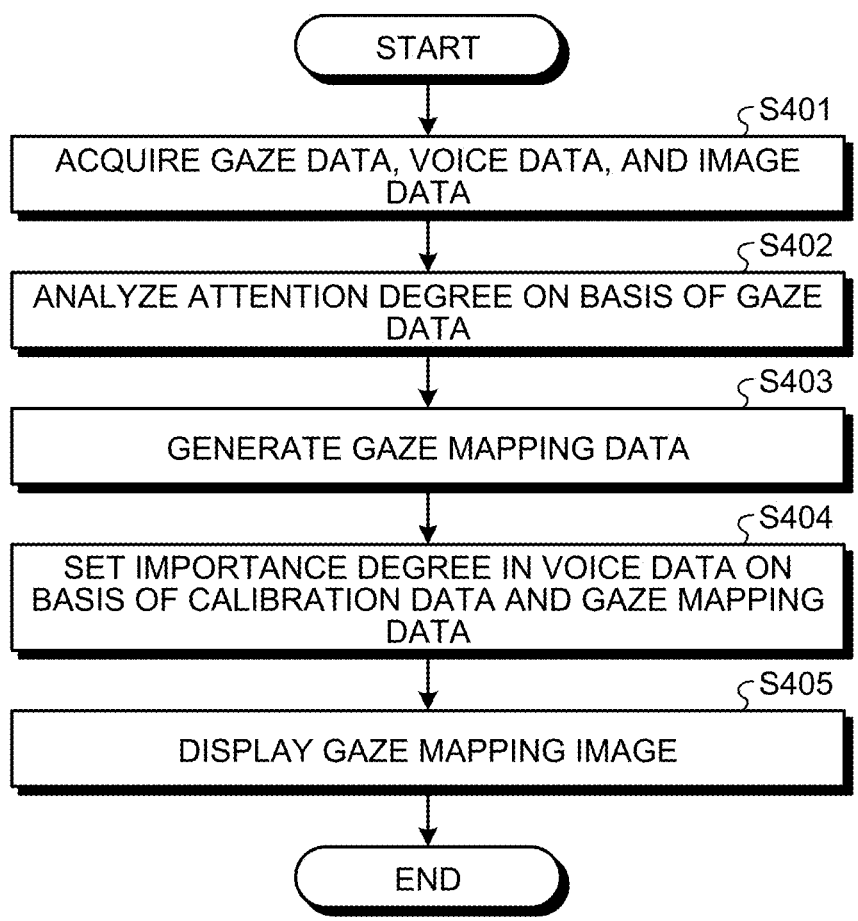
FIG. 13 is a flowchart illustrating an outline of processing that is executed by the information processing apparatus according to the modification example of the third embodiment of the present disclosure.

Next, processing that is executed by the information processing apparatus 100a will be described. FIG. 13 is a flowchart illustrating the outline of the processing that is executed by the information processing apparatus 100a. In FIG. 13, Step S401 and Step S402 respectively correspond to Step S301 and Step S302 of FIG. 9 described above. In addition, Step S403 corresponds to Step S304 of FIG. 9 described above.

In Step S404, the setting unit 112 performs setting of assigning the importance degree according to the calibration data and the attention degree to the voice data on the basis of the gaze mapping data in which the calibration data that is recorded in the calibration data storage unit 116 and the attention degree of the user that is generated by the generating unit 113 are associated with the image to be recorded in the recording unit 114. After Step S404, the information processing apparatus 100a proceeds to Step S405. Step S405 corresponds to Step S305 of FIG. 9 described above.

According to the modification example of the third embodiment described above, the setting unit 112 performs the setting of assigning the importance degree according to the attention degree to the voice data at each predetermined time interval on the basis of the gaze mapping data in which the attention degree of the user that is generated by the generating unit 113 is associated with the image to be recorded in the recording unit 114, and thus, it is possible to grasp which period of the voice data is important.

In addition, in the third embodiment and the modification example of the third embodiment, an embodiment in which an importance degree of voice and speaking is applied will be described by using the attention degree and the calibration data. As a modification example thereof, in order to extract the period of the gaze data corresponding to the important voice period that is a period in which a predetermined word (keyword) is output (or the area and the position of the image after being mapped to the image) by using the important voice period and the calibration data acquired in advance.

Fourth Embodiment

Next, a fourth embodiment of the present disclosure will be described. In the third embodiment, each of the gaze data and the voice data is input externally, but in the fourth embodiment, the gaze data and the voice data are generated. Hereinafter, the configuration of an information processing apparatus according to the fourth embodiment will be described, and then, processing that is executed by the information processing apparatus according to the fourth embodiment will be described. Furthermore, the same reference numerals will be applied to the same configurations as those of the information processing system 1c according to the third embodiment described above, and the detailed description will be suitably omitted.

Configuration of Information Processing Apparatus

Figure 14:
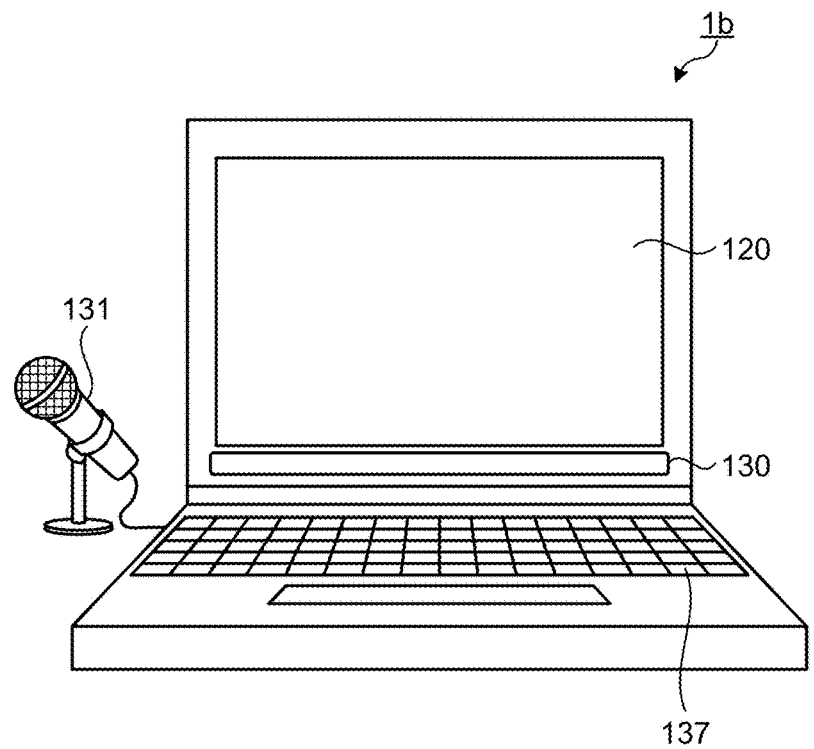
FIG. 14 is a schematic view illustrating a configuration of an information processing apparatus according to a fourth embodiment of the present disclosure.
Figure 15:
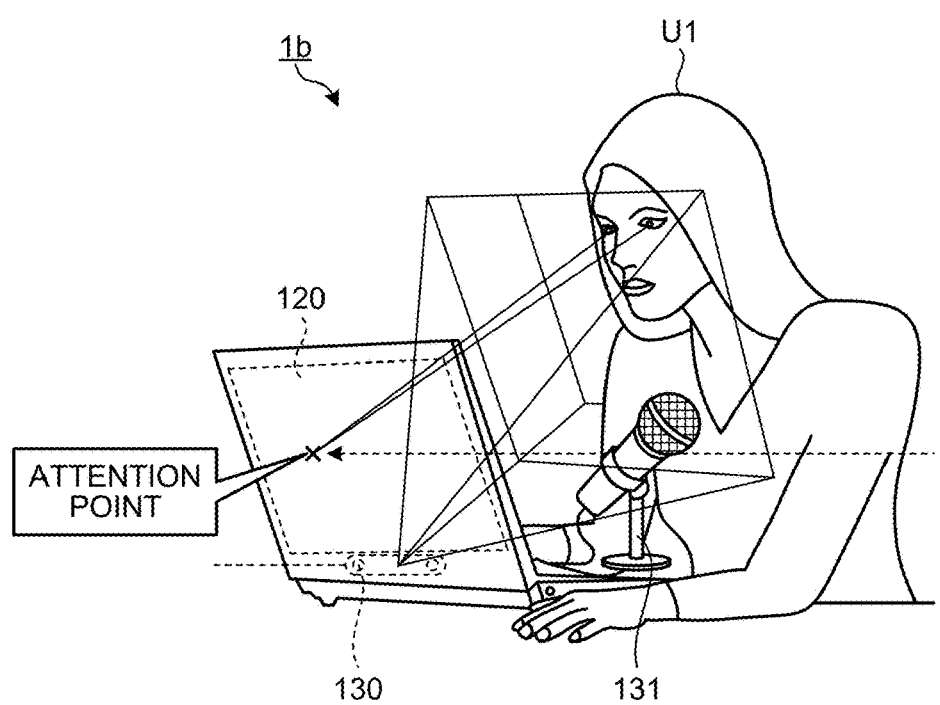
FIG. 15 is a schematic view illustrating the configuration of the information processing apparatus according to the fourth embodiment of the present disclosure.
Figure 16:
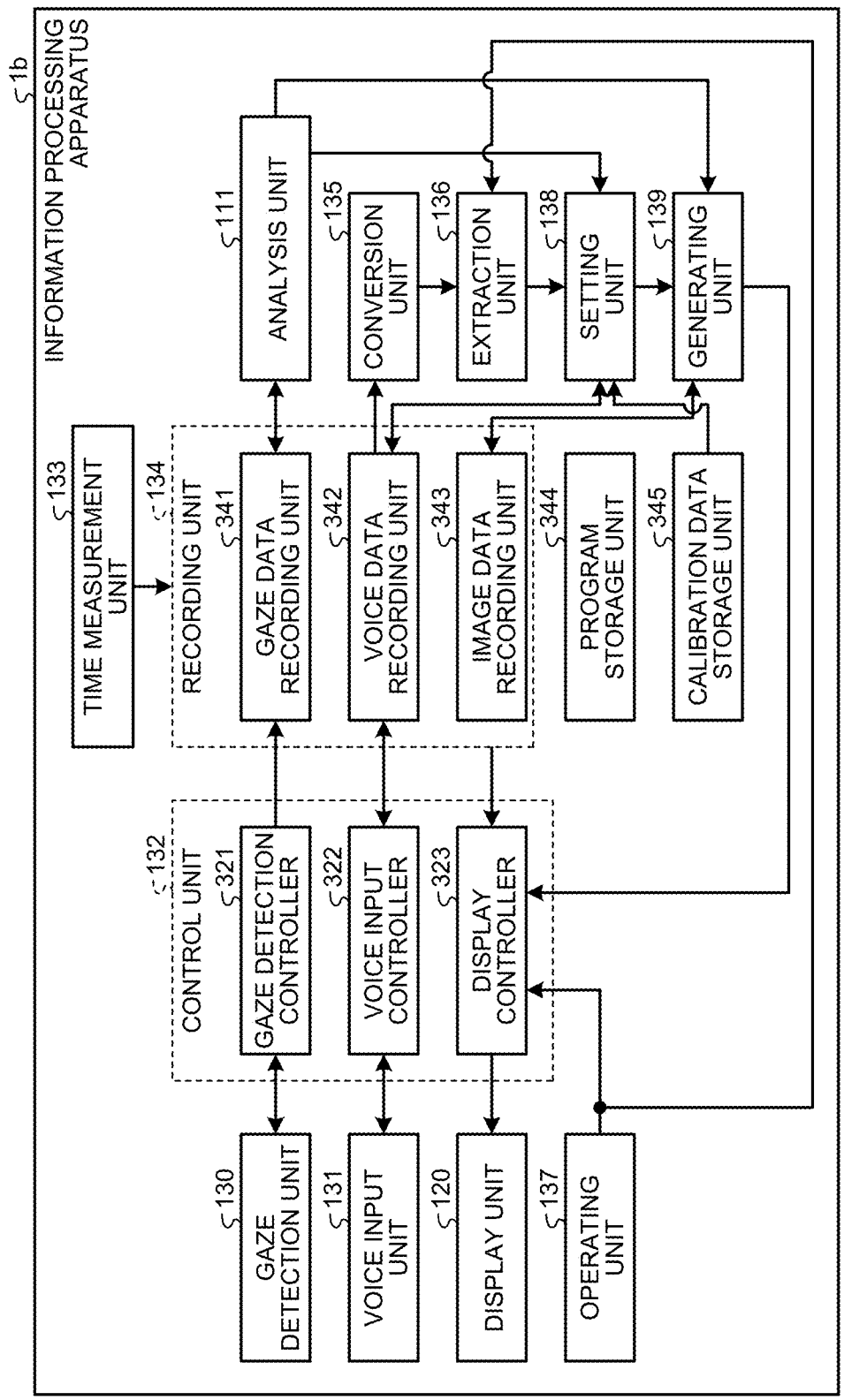
FIG. 16 is a block diagram illustrating a functional configuration of the information processing apparatus according to the fourth embodiment of the present disclosure.

FIG. 14 is a schematic view illustrating the configuration of the information processing apparatus according to the fourth embodiment. FIG. 15 is a schematic view illustrating the configuration of the information processing apparatus according to the fourth embodiment. FIG. 16 is a block diagram illustrating a functional configuration of the information processing apparatus according to the fourth embodiment.

An information processing apparatus 1b illustrated in FIG. 14 to FIG. 16 includes the analysis unit 111, the display unit 120, a gaze detection unit 130, a voice input unit 131, a control unit 132, a time measurement unit 133, the recording unit 134, a conversion unit 135, an extraction unit 136, an operating unit 137, a setting unit 138, a generating unit 139, a program storage unit 344, and a calibration data storage unit 345.

The gaze detection unit 130 is configured by using an LED light source that emits a near infrared ray, and an optical sensor (for example, a CMOS, a CCD, or the like) that captures a pupil point and a reflex point on the cornea. The gaze detection unit 130 is provided on a side surface of a housing of the information processing apparatus 1b on which the display unit 120 is visible to the user U1 (refer to FIG. 14 and FIG. 15). The gaze detection unit 130 generates gaze data in which the gaze of the user U1 with respect to the image that is displayed on the display unit 120 is detected, and outputs the gaze data to the control unit 132, under the control of the control unit 132. Specifically, the gaze detection unit 130 generates the gaze data by irradiating the cornea of the user U1 with a near infrared ray from the LED light source or the like, and by capturing the pupil point and the reflex point on the cornea of the user U1 with the optical sensor, under the control of the control unit 132. Then, the gaze detection unit 130 generates gaze data of a predetermined time by continuously calculating the gaze of the user or the gaze from the pattern of the pupil point and the reflex point of the user U1, on the basis of an analysis result analyzed by performing image processing or the like with respect to the data that is generated by the optical sensor, and outputs the gaze data to a gaze detection controller 321 described below, under the control of the control unit 132. Furthermore, the gaze detection unit 130 may generate the gaze data in which the gaze of the user U1 is detected by simply detecting the pupil of the user U1 only with the optical sensor by using known pattern matching, or may generate the gaze data by detecting the gaze of the user U1 by using other sensors or other known technologies.

The voice input unit 131 is configured by using a microphone to which a voice is input, and a voice codec that converts the voice of which the input is received by the microphone into digital voice data, and outputs the voice data to the control unit 132 by amplifying the voice data. The voice input unit 131 generates the voice data by receiving the input of the voice of the user U1, and outputs the voice data to the control unit 132, under the control of the control unit 132. Furthermore, the voice input unit 131 may be provided with a voice output function by including a speaker or the like that is capable of outputting a voice, in addition to the input of the voice.

The control unit 132 is configured by using a CPU, an FPGA, a GPU, and the like, and controls the gaze detection unit 130, the voice input unit 131, and the display unit 120. The control unit 132 includes a gaze detection controller 321, a voice input controller 322, and a display controller 323.

The gaze detection controller 321 controls the gaze detection unit 130. Specifically, the gaze detection controller 321 allows the gaze detection unit 130 to generate the gaze data by irradiating the user U1 with a near infrared ray at each predetermined timing, and by capturing the pupil of the user U1. In addition, the gaze detection controller 321 performs various pieces of image processing with respect to gaze data that is input from the gaze detection unit 130, and outputs the gaze data to the recording unit 134.

The voice input controller 322 controls the voice input unit 131, performs various pieces of processing, for example, gain-up processing, noise reduction processing, or the like with respect to the voice data that is input from the voice input unit 131, and outputs the voice data to the recording unit 134.

The display controller 323 controls a display mode of the display unit 120. The display controller 323 allows the display unit 120 to display an image corresponding to the image data that is recorded in the recording unit 134 or a gaze mapping image corresponding to the gaze mapping data that is generated by the generating unit 139.

The time measurement unit 133 is configured by using a timer, a clock generator, or the like, and applies the time information to the gaze data that is generated by the gaze detection unit 130, the voice data that is generated by the voice input unit 131, and the like.

The recording unit 134 is configured by using a volatile memory, a non-volatile memory, a recording medium, and the like, and records various information items relevant to the information processing apparatus 1b. The recording unit 134 includes a gaze data recording unit 341, a voice data recording unit 342, and an image data recording unit 343.

The gaze data recording unit 341 records the gaze data that is input from the gaze detection controller 321, and outputs the gaze data to the analysis unit 111.

The voice data recording unit 342 records the voice data that is input from the voice input controller 322, and outputs the voice data to the conversion unit 135.

The image data recording unit 343 records a plurality of image data items. The plurality of image data items are data that is input externally of the information processing apparatus 1b, or data that is captured by an external imaging device in a recording medium.

The program storage unit 344 stores various programs that are executed by the information processing apparatus 1b, data that is used during the execution of various programs (for example, dictionary information or text conversion dictionary information), and processing data during the execution of various programs.

The calibration data storage unit 345 stores the calibration data for each user.

The conversion unit 135 performs known text conversion processing with respect to the voice data, and thus, converts the voice data into the character information (the text data), and outputs the character information to the extraction unit 136. Furthermore, character conversion of the voice may not be performed at this time point, and at this time, the importance degree may be set as voice information, and then, may be converted into the character information.

The extraction unit 136 extracts a character or a word (a keyword) corresponding to the instruction signal that is input from the operating unit 137 described below, from the character information that is converted by the conversion unit 135, and outputs an extraction result to the setting unit 138. Furthermore, in a case where the instruction signal is not input from the operating unit 137 described below, the extraction unit 136 outputs the character information as is input from the conversion unit 135 to the setting unit 138.

The operating unit 137 is configured by using a mouse, a keyboard, a touch panel, various switches, and the like, receives the input of the operation of the user U1, and outputs operation contents of which the input is received to the control unit 132.

The setting unit 138 assigns the importance degree and the character information that is converted by the conversion unit 135 to the voice data associated with a time axis identical to that of the gaze data, on the basis of the calibration data that is recorded in the calibration data storage unit 345, the attention degree that is analyzed by the analysis unit 111 at each predetermined time interval, and the character information that is extracted by the extraction unit 136 to be recorded in the recording unit 134.

The generating unit 139 generates the gaze mapping data in which the attention degree that is analyzed by the analysis unit 111 and the character information that is converted by the conversion unit 135 are associated with the image corresponding to the image data that is displayed on the display unit 120, and outputs the gaze mapping data to the image data recording unit 343 or the display controller 323.

Processing of Information Processing Apparatus

Figure 17:
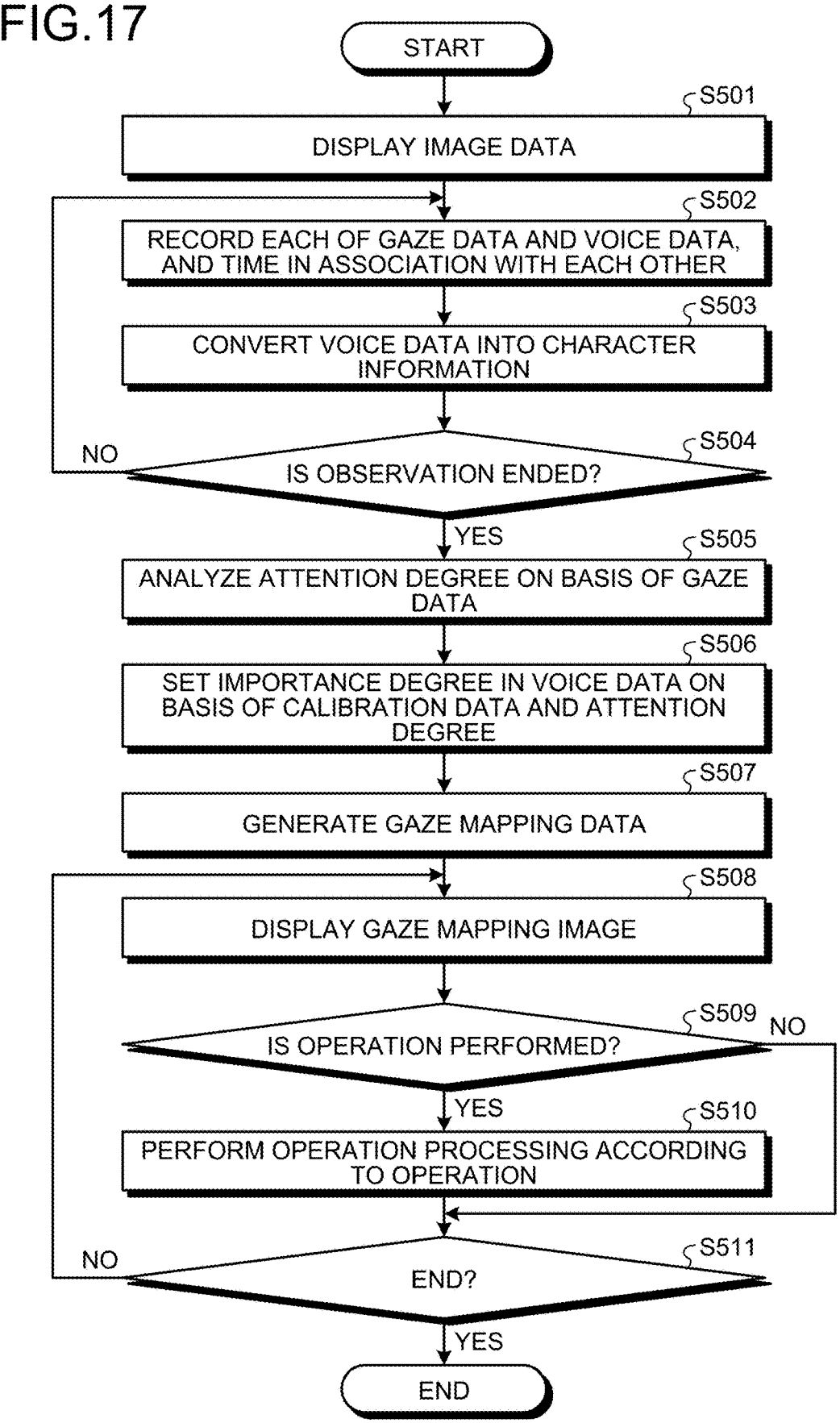
FIG. 17 is a flowchart illustrating an outline of processing that is executed by the information processing apparatus according to the fourth embodiment of the present disclosure.

Next, processing that is executed by the information processing apparatus 1b will be described. FIG. 17 is a flowchart illustrating the outline of the processing that is executed by the information processing apparatus 1b.

As illustrated in FIG. 17, first, the display controller 323 allows the display unit 120 to display the image corresponding to the image data that is recorded in the image data recording unit 343 (Step S501). In this case, the display controller 323 allows the display unit 120 to display an image corresponding to image data that is selected according to the operation of the operating unit 137.

Subsequently, the control unit 132 associates each of the gaze data that is generated by the gaze detection unit 130 and the voice data that is generated by the voice input unit 131 with the time that is measured by the time measurement unit 133 to be recorded in the gaze data recording unit 341 and the voice data recording unit 342 (Step S502).

After that, the conversion unit 135 converts the voice data that is recorded in the voice data recording unit 342 into the character information (Step S503). Furthermore, such a step may be performed after Step S506 described below.

Subsequently, in a case where an instruction signal of ending the observation of the image that is displayed on the display unit 120 is input from the operating unit 137 (Step S504: Yes), the information processing apparatus 1b proceeds to Step S505 described below. In contrast, in a case where the instruction signal of ending the observation of the image that is displayed on the display unit 120 is not input from the operating unit 137 (Step S504: No), the information processing apparatus 1b returns to Step S502.

Step S505 corresponds to Step S302 of FIG. 9 described above. After Step S505, the information processing apparatus 1b proceeds to Step S506 described below.

In Step S506, the setting unit 138 assigns the importance degree and the character information that is converted by the conversion unit 135 to the voice data which a time axis identical to that of the gaze data is associated, on the basis of the calibration data that is recorded in the calibration data storage unit 345, the attention degree that is analyzed by the analysis unit 111, and the character information that is extracted by the extraction unit 136 to be recorded in the recording unit 134. In this case, the setting unit 138 corrects a time lag between the attention period of the gaze and a voice pronunciation time when a voice is pronounced by using calibration corresponding to the user U1, and then, performs the weighting of the importance degree of the voice data corresponding to the character information that is extracted by the extraction unit 136 to be recorded in the recording unit 134. For example, the setting unit 138 assigns a value obtained by multiplying a coefficient based on the character information that is extracted by the extraction unit 136 and the attention degree together to the voice data, as the importance degree to be recorded in the recording unit 134.

Subsequently, the generating unit 139 generates the gaze mapping data in which the attention degree that is analyzed by the analysis unit 111 and the character information that is converted by the conversion unit 135 are associated with the image corresponding to the image data that is displayed on the display unit 120 (Step S507).

Subsequently, the display controller 323 allows the display unit 120 to display the gaze mapping image corresponding to the gaze mapping data that is generated by the generating unit 139 (Step S508).

Figure 18:
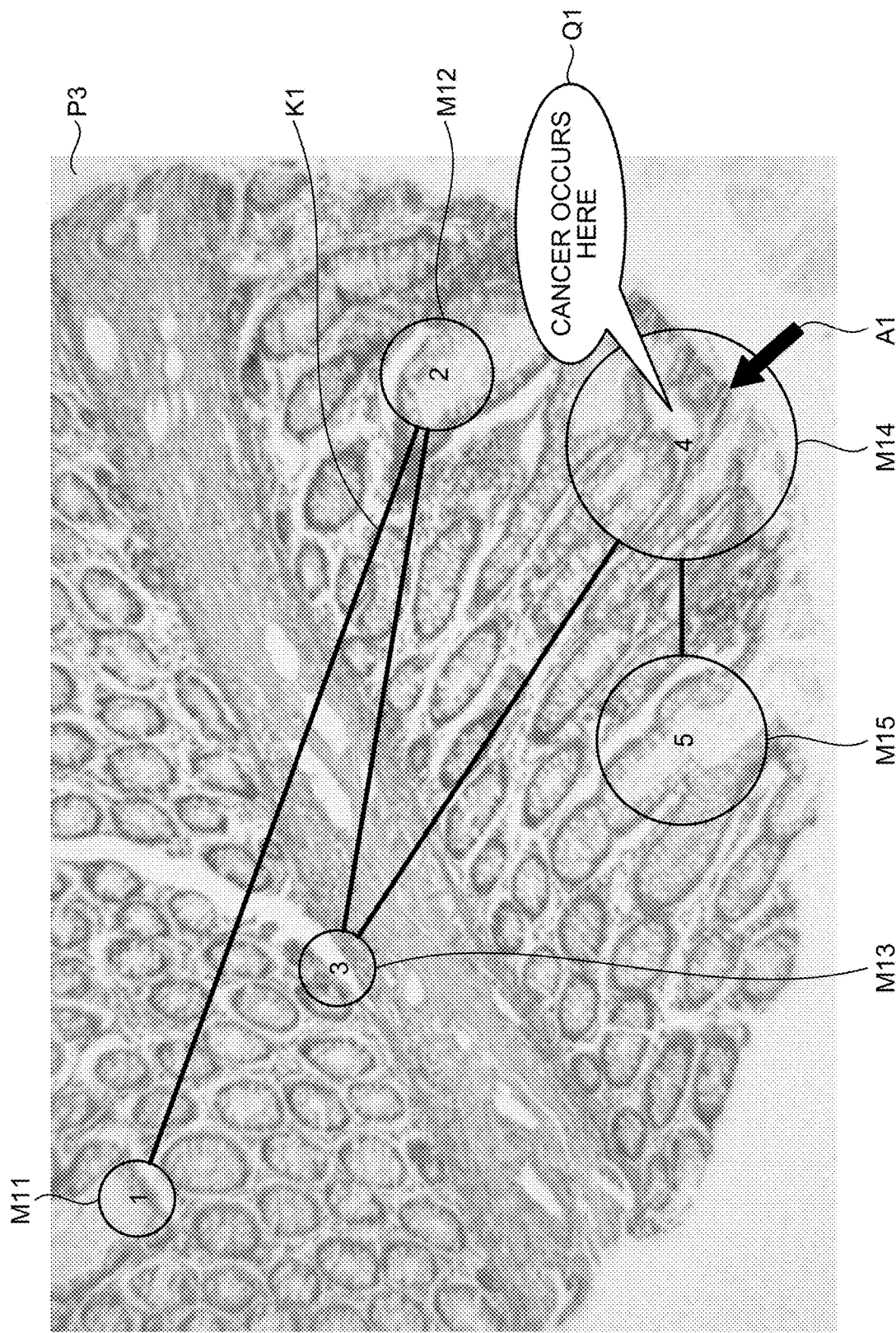
FIG. 18 is a diagram illustrating an example of a gaze mapping image that is displayed on a display unit according to the fourth embodiment of the present disclosure.

FIG. 18 is a diagram illustrating an example of the gaze mapping image that is displayed on the display unit 120. As illustrated in FIG. 18, the display controller 323 allows the display unit 120 to display a gaze mapping image P3 corresponding to the gaze mapping data that is generated by the generating unit 113. The marks M11 to M15 corresponding to the attention area of the gaze and the locus K1 of the gaze are superimposed on the gaze mapping image P3, and the character information of the voice data that is output at the timing of the attention degree is associated with the gaze mapping image P3. In addition, in the marks M11 to M15, the number indicates the order of the gaze of the user U1, and the size (the area) indicates the attention degree. Further, in a case where the user U1 moves a cursor A1 to a desired position by operating the operating unit 137, for example, to the mark M14, character information Q1 that is associated with the mark M14, for example, "Cancer Occurs Here." is displayed. Furthermore, in FIG. 18, the display controller 323 allows the display unit 120 to display the character information, but for example, may output the voice data by converting the character information into a voice. Accordingly, the user U1 is capable of intuitively grasping important voice contents and an area at which the user gazes. Further, it is possible to intuitively grasp the locus of the gaze in the observation of the user U1.

Figure 19A:
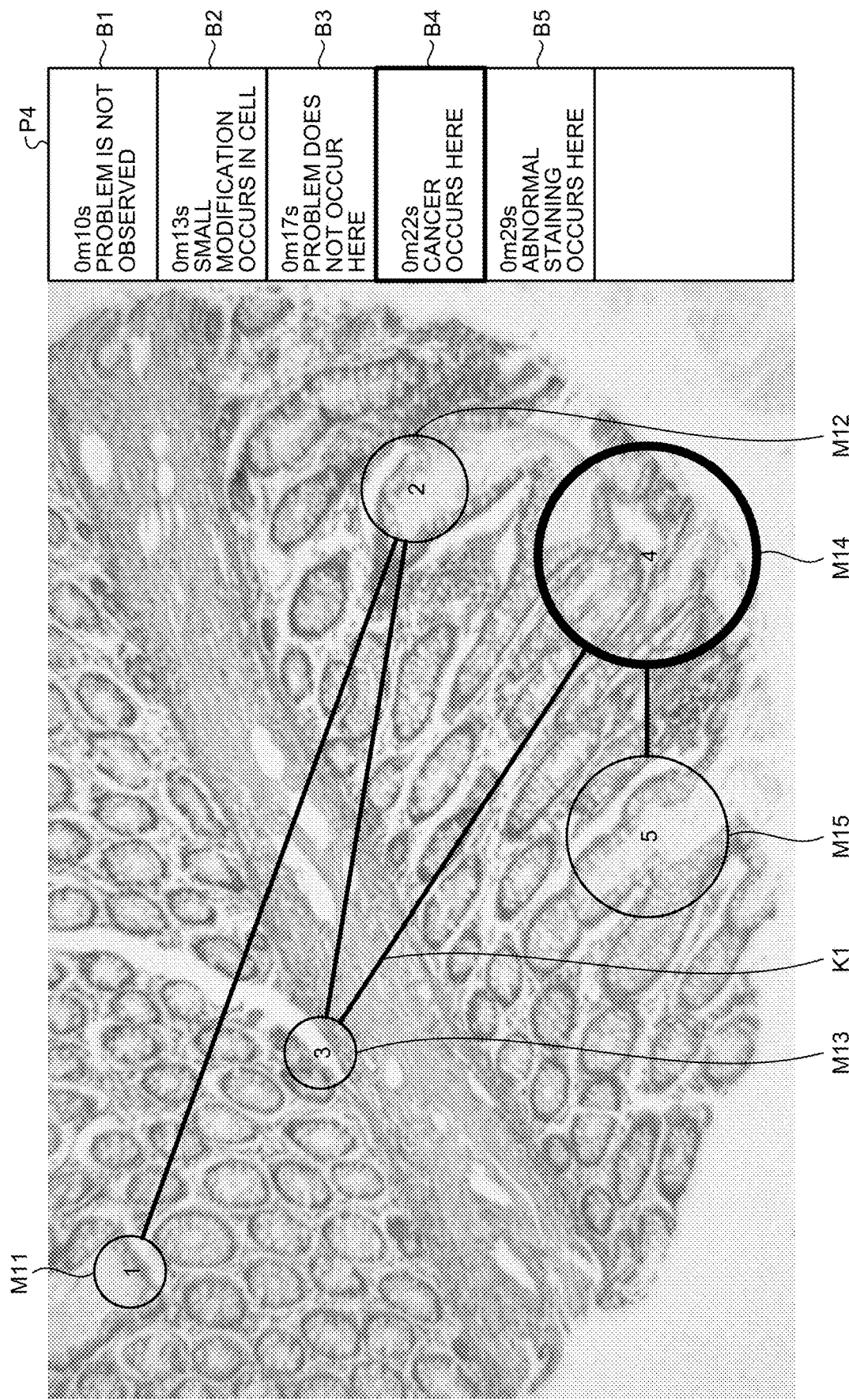
FIG. 19A is a diagram illustrating another example of the gaze mapping image that is displayed on the display unit according to the fourth embodiment of the present disclosure.

FIG. 19A is a diagram illustrating another example of the gaze mapping image that is displayed on the display unit 120. As illustrated in FIG. 19A, the display controller 323 allows the display unit 120 to display the gaze mapping data P4 corresponding to the gaze mapping data that is generated by the generating unit 139. Further, the display controller 323 allows the display unit 120 to display icons B1 to B5 in which the character information is associated with a time when the character information is pronounced. Further, in a case where the user U1 selects any one of the marks M11 to M15 by operating the operating unit 137, for example, selects the mark M14, the display controller 323 allows the display unit 120 to highlight-display the mark M14, and allows the display unit 120 to highlight-displayed the character information corresponding to the time of the mark M14, for example, the icon B4 (for example, to highlight-display or display a frame by a bold line). Accordingly, the user U1 is capable of intuitively grasping important voice contents and an area at which the user gazes, and of intuitively grasping the contents at the time of being pronounced.

In addition, the gaze data that is the basis of the attention degree, and the voice data that is the basis of the character information are corrected by the calibration data, and thus, the time lag decreases compared to that before the correction. For this reason, in a case where the user pronounces a portion including an image while gazing the portion, a temporally overlapping ratio between a period in which the attention degree of the gaze data is assigned and a period in which the importance degree of the voice data is assigned increases compared to that before the correction. Based on this, the generating unit 139 generates data having a format in which the gaze data in the gaze mapping data and the voice data are associated with each other by a time.

FIG. 19B is an example of the data in which the gaze data and the voice data are associated with each other by the time, and illustrates the contents of a data format of the data. In Table T1 of FIG. 19B, a start time and an end time of the gaze data, and a start time and an end time of the voice data are associated with each other according to an Index number.

Accordingly, as shown in Table T1 of FIG. 19B, for example, the generating unit 139 is capable of taking out gaze data by the Index number, and of taking out the corresponding voice data. In contrast, the generating unit 139 is also capable of taking out information of (the gaze data) of which part of the image the user gazes at that time from the period in which the voice is output (the important voice period), by the Index number. On the contrary, the generating unit 139 is also capable of taking out the voice (the character information) that is seen and output from the attention position (area) of the gaze in an observation image, by the Index number, and of visualizing and presenting the character information corresponding to the attention position. As a method other than the method described above, the generating unit 139 may associate a temporal change in a feature data (the moving distance and the residence time) of the gaze with the voice data.

Returning to FIG. 17, Step S509 and the subsequence will be continuously described.

In Step S509, any one of the marks corresponding to a plurality of attention areas is operated by the operating unit 137 (Step S509: Yes), the control unit 132 executes operation processing according to the operation (Step S510). Specifically, the display controller 323 allows the display unit 120 to highlight-display the mark corresponding to the attention area that is selected by the operating unit 137 (for example, refer to FIG. 18). In addition, the voice input controller 322 allows the voice input unit 131 to reproduce the voice data that is associated with an area having a high attention degree. After Step S510, the information processing apparatus 1b proceeds to Step S511 described below.

In Step S509, in a case where any one of the marks corresponding to the plurality of attention degree areas is not operated by the operating unit 137 (Step S509: No), the information processing apparatus 1b proceeds to Step S511 described below.

In Step S511, in a case where an instruction signal of instructing the end of the observation is input from the operating unit 137 (Step S511: Yes), the information processing apparatus 1b ends this processing. In contrast, in a case where the instruction signal of instructing the end of the observation is not input from the operating unit 137 (Step S511: No), the information processing apparatus 1b returns to Step S508 described above.

According to the fourth embodiment described above, the generating unit 139 generates the gaze mapping data in which the attention degree that is analyzed by the analysis unit 111 and the character information that is converted by the conversion unit 135 are associated with the image corresponding to the image data that is displayed on the display unit 120, and thus, the user U1 is capable of intuitively grasping important voice contents and an area at which the user gazes, and of intuitively grasping the contents at the time of being pronounced.

In addition, according to the fourth embodiment, the display controller 323 allows the display unit 120 to display the gaze mapping image corresponding to the gaze mapping data that is generated by the generating unit 139, and thus, can be used in the confirmation of preventing the observation of the user with respect to the image from being missed, the confirmation of technical skill such as diagnostic interpretation of the user, and the education, the conference, and the like of the diagnostic interpretation, the observation, or the like with respect to other users.

Fifth Embodiment

Next, a fifth embodiment of the present disclosure will be described. In the fourth embodiment described above, only the information processing apparatus 1b is provided, but in the fifth embodiment, the information processing apparatus is incorporated in a part of the microscope system. Hereinafter, the configuration of a microscope system according to the fifth embodiment will be described, and then, processing that is executed by the microscope system according to the fifth embodiment will be described. Furthermore, the same reference numerals will be applied to the same configurations as those of the information processing apparatus 1b according to the fourth embodiment described above, and the detailed description will be suitably omitted.

Configuration of Microscope System

Figure 20:
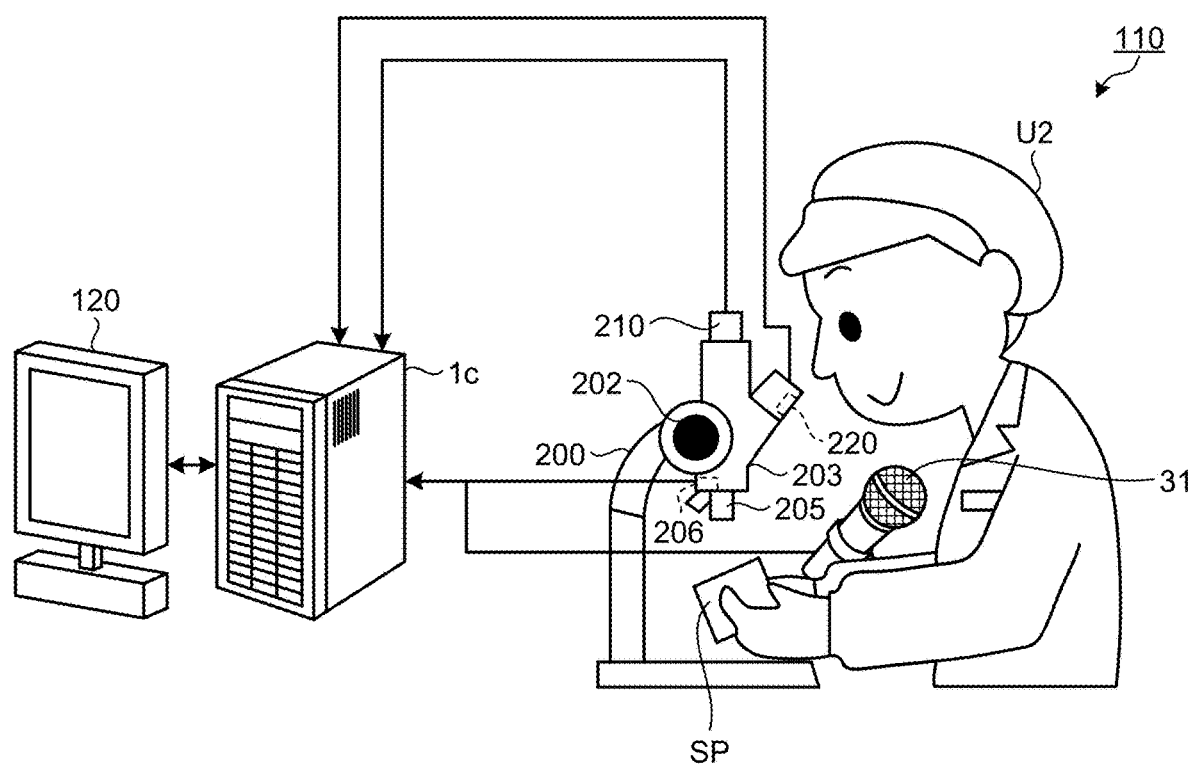
FIG. 20 is a schematic view illustrating a configuration of a microscope system according to a fifth embodiment of the present disclosure.
Figure 21:
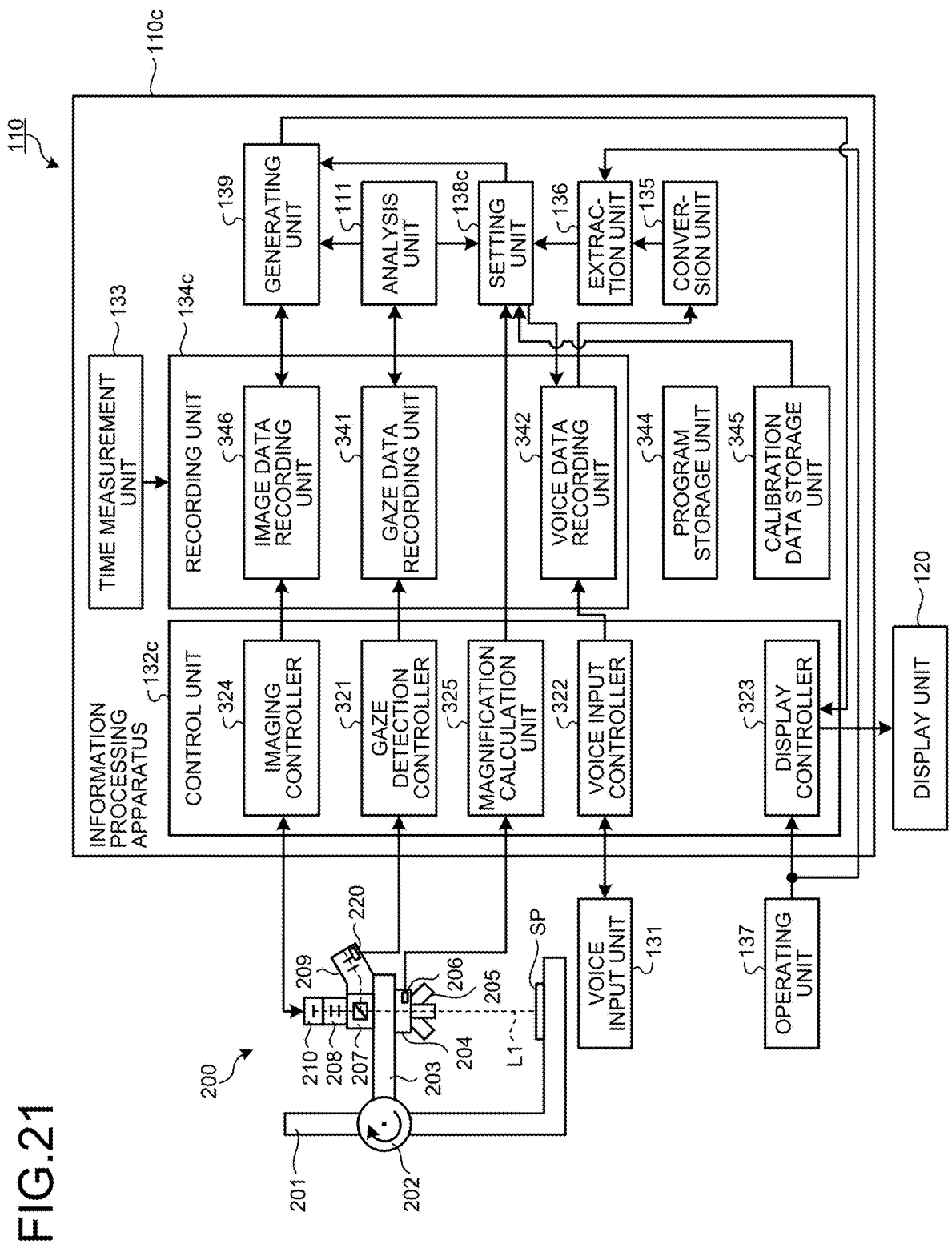
FIG. 21 is a block diagram illustrating a functional configuration of the microscope system according to the fifth embodiment of the present disclosure.

FIG. 20 is a schematic view illustrating the configuration of the microscope system according to the fifth embodiment. FIG. 21 is a block diagram illustrating a functional configuration of the microscope system according to the fifth embodiment.

As illustrated in FIG. 20 and FIG. 21, a microscope system 110 includes an information processing apparatus 110c, a display unit 120, a voice input unit 131, an operating unit 137, a microscope 200, an imaging unit 210, and a gaze detection unit 220.

Configuration of Microscope

First, the configuration of the microscope 200 will be described.

The microscope 200 includes a main body portion 201, a rotation portion 202, an elevating portion 203, a revolver 204, an objective lens 205, a magnification detection unit 206, a lens barrel portion 207, a connection portion 208, and an eyepiece portion 209.

A specimen SP is mounted on the main body portion 201. The main body portion 201 is approximately in the shape of U, and the elevating portion 203 is connected to the main body portion 201 by using the rotation portion 202.

The rotation portion 202 is rotated according to the operation of a user U2, and thus, moves the elevating portion 203 in a vertical direction.

The elevating portion 203 is provided to be movable in the vertical direction with respect to the main body portion 201. In the elevating portion 203, the revolver 204 is connected to a surface on one end side, and the lens barrel portion 207 is connected to a surface on the other end side.

A plurality of objective lenses 205 having magnifications different from each other are connected to the revolver 204, and the revolver 204 is rotatively connected to the elevating portion 203 with respect to an optical axis L1. The revolver 204 arranges a desired objective lens 205 on the optical axis L1 according to the operation of a user U2. Furthermore, information indicating the magnification, for example, an IC chip or a label is attached to the plurality of objective lenses 205. Furthermore, a shape indicating the magnification may be provided in the objective lens 205, in addition to the IC chip or the label.

The magnification detection unit 206 detects the magnification of the objective lens 205 that is arranged on the optical axis L1, and outputs a detection result thereof to the information processing apparatus 110c. The magnification detection unit 206, for example, includes a unit detecting the position of the objective switching revolver 204.

The lens barrel portion 207 transmits a part of a subject image of the specimen SP that is formed by the objective lens 205 through the connection portion 208 to be reflected on the eyepiece portion 209. The lens barrel portion 207 includes a prism, a half mirror, a collimator lens, and the like inside.

In the connection portion 208, one end is connected to the lens barrel portion 207, and the other end is connected to the imaging unit 210. The connection portion 208 guides the subject image of the specimen SP that is transmitted through the lens barrel portion 207 to the imaging unit 210. The connection portion 208 is configured by using a plurality of collimator lenses and imaging lenses, and the like.

The eyepiece portion 209 forms an image by guiding the subject image that is reflected on the lens barrel portion 207. The eyepiece portion 209 is configured by using a plurality of collimator lenses and imaging lenses, and the like.

Configuration of Imaging Unit

Next, the configuration of the imaging unit 210 will be described.

The imaging unit 210 generates the image data by receiving the subject image of the specimen SP that is formed by the connection portion 208, and outputs the image data to the information processing apparatus 110c. The imaging unit 210 is configured by using an image sensor such as a CMOS or a CCD, an image processor performing various pieces of image processing with respect to the image data, and the like.

Configuration of Gaze Detection Unit

Next, the configuration of the gaze detection unit 220 will be described.

The gaze detection unit 220 is provided inside or outside the eyepiece portion 209, generates the gaze data by detecting the gaze of the user U2, and outputs the gaze data to the information processing apparatus 110c. The gaze detection unit 220 is configured by using an LED light source that is provided inside the eyepiece portion 209, and emits a near infrared ray, an optical sensor that is provided inside the eyepiece portion 209, and captures the pupil point and the reflex point on the cornea (for example, a CMOS and a CCD). The gaze detection unit 220 irradiates the cornea of the user U2 with a near infrared ray from the LED light source or the like, and generates the gaze data by capturing the pupil point and the reflex point on the cornea of the user U2 with the optical sensor, under the control of the information processing apparatus 110c. Then, the gaze detection unit 220 generates the gaze data by detecting the gaze of the user from the pattern of a pupil point and a reflex point of the user U2, and outputs the gaze data to the information processing apparatus 110c, on the basis of an analysis result analyzed by image processing or the like with respect to the data that is generated by the optical sensor, under the control of the information processing apparatus 110c.

Configuration of Information Processing Apparatus

Next, the configuration of the information processing apparatus 110c will be described.

The information processing apparatus 110c includes a control unit 132c, a recording unit 34c, and a setting unit 138c, instead of the control unit 132, the recording unit 34, and the setting unit 138 of the information processing apparatus 1b according to the fourth embodiment described above.

The control unit 132c is configured by using a CPU, an FPGA, a GPU, and the like, and controls the display unit 120, the voice input unit 131, the imaging unit 210, and the gaze detection unit 220. The control unit 132c further includes an imaging controller 324 and a magnification calculation unit 325, in addition to the gaze detection controller 321, the voice input controller 322, and the display controller 323 of the control unit 132 of the fourth embodiment described above.

The imaging controller 324 controls the operation of the imaging unit 210. The controller 324 generates the image data by allowing the imaging unit 210 to sequentially perform capturing according to a predetermined frame rate. The controller 324 performs image processing (for example, developing processing or the like) with respect to the image data that is input from the imaging unit 210, and outputs the image data to the recording unit 134c.

The magnification calculation unit 325 calculates an observation magnification of the current microscope 200, and outputs a calculation result to the setting unit 138c, on the basis of a detection result that is input from the magnification detection unit 206. For example, the magnification calculation unit 325 calculates the observation magnification of the current microscope 200 on the basis of the magnification of the objective lens 205 that is input from the magnification detection unit 206 and the magnification of the eyepiece portion 209.

The recording unit 134c is configured by using a volatile memory, a non-volatile memory, a recording medium, and the like. The recording unit 134c includes an image data recording unit 346, instead of the image data recording unit 343 according to the fourth embodiment described above. The image data recording unit 346 records the image data that is input from the imaging controller 324, and outputs the image data to the generating unit 139.

The setting unit 138c assigns the importance degree and the character information that is converted by the conversion unit 135 to the voice data associated with a time axis identical to that of the gaze data to be recorded in the recording unit 134c, on the basis of the calibration data that is recorded in the calibration data storage unit 345, the attention degree that is analyzed by the analysis unit 111, and the calculation result that is calculated by the magnification calculation unit 325. Specifically, the setting unit 138c assigns a value obtained multiplied by a coefficient based on the calculation result that is calculated by the magnification calculation unit 325, to the attention degree that is analyzed by the analysis unit 111, as the importance degree (for example, a numerical value) for each frame of the voice data to be recorded in the recording unit 134c. That is, the setting unit 138c performs processing increasing the importance degree as the display magnification increases. The setting unit 138c is configured by using a CPU, an FPGA, a GPU, and the like.

Processing of Microscope System

Figure 22:
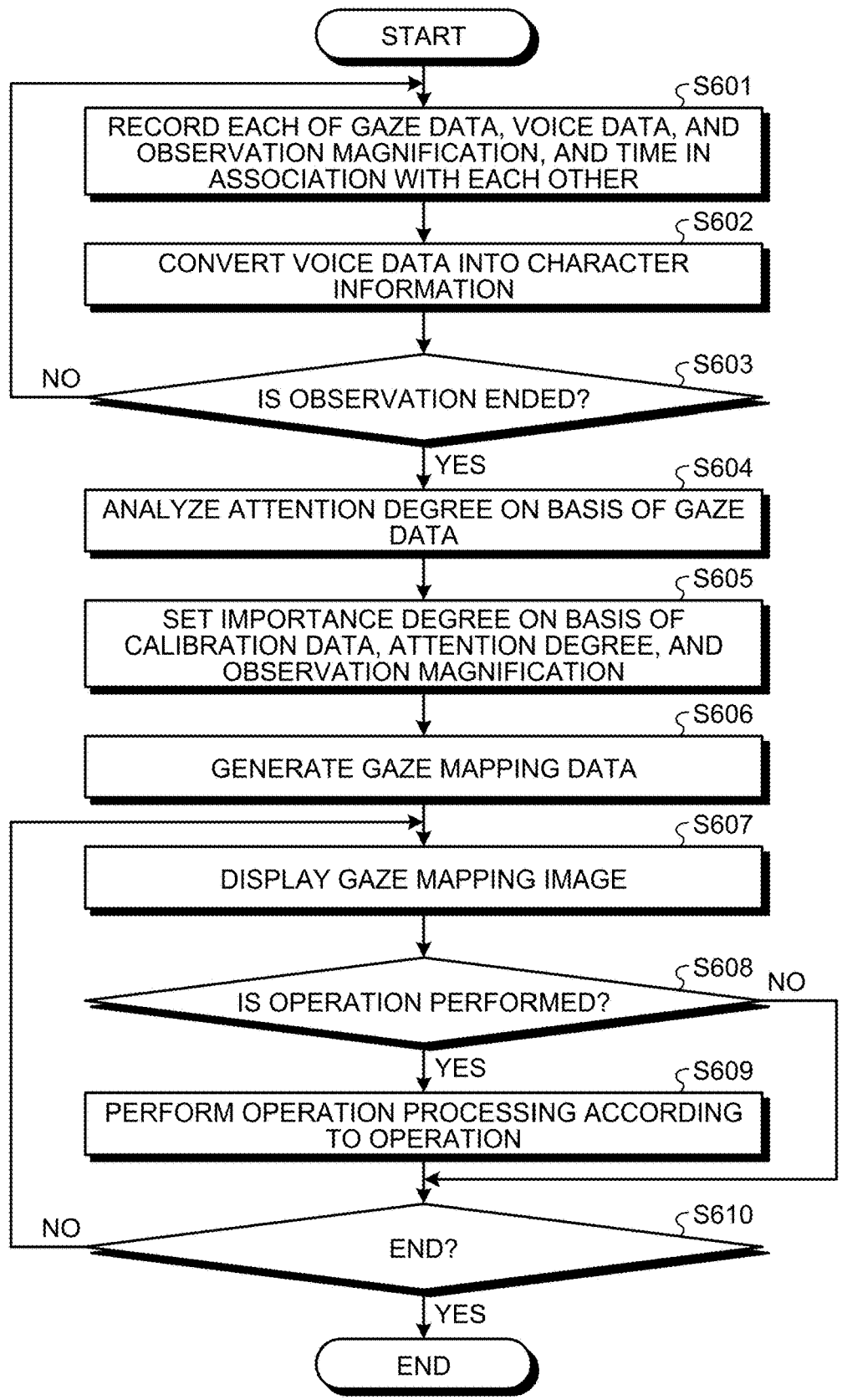
FIG. 22 is a flowchart illustrating an outline of processing that is executed by the microscope system according to the fifth embodiment of the present disclosure.

Next, processing that is executed by the microscope system 110 will be described. FIG. 22 is a flowchart illustrating the outline of the processing that is executed by the microscope system 110.

As illustrated in FIG. 22, first, the control unit 132c associates each of the gaze data that is generated by the gaze detection unit 220, the voice data that is generated by the voice input unit 131, and the observation magnification that is calculated by the magnification calculation unit 325 with the time that is measured by the time measurement unit 133 to be recorded in the gaze data recording unit 341 and the voice data recording unit 342 (Step S601). After Step S601, the microscope system 110 proceeds to Step S602 described below.

Step S602 to Step S604 respectively correspond to Step S503 to Step S505 of FIG. 17 described above. After Step S604, the microscope system 110 proceeds to Step S605.

In Step S605, the setting unit 138c assigns the importance degree and the character information that is converted by the conversion unit 135 to the voice data associated with a time axis identical to that of the gaze data, on the basis of the calibration data that is recorded in the calibration data storage unit 345, the attention degree that is analyzed by the analysis unit 111 at each predetermined time interval, and the calculation result that is calculated by the magnification calculation unit 325 to be recorded in the recording unit 134c. After Step S605, the microscope system 110 proceeds to Step S606.

Step S606 to Step S610 respectively correspond to Step S507 to Step S511 of FIG. 17 described above.

According to the fifth embodiment described above, the setting unit 138c assigns the importance degree and the character information that is converted by the conversion unit 135 to the voice data associated with a time axis identical to that of the gaze data, on the basis of the calibration data that is recorded in the calibration data storage unit 345, the attention degree that is analyzed by the analysis unit 111, and the calculation result that is calculated by the magnification calculation unit 325 to be recorded in the recording unit 134c, and thus, the importance degree based on the observation magnification and the attention degree is assigned to the voice data, and therefore, it is possible to grasp an important period of the voice data to which the observation contents and the attention degree are added.

Furthermore, in the fifth embodiment, the observation magnification that is calculated by the magnification calculation unit 325 is recorded in the recording unit 114, but operation history of the user U2 may be recorded, and the importance degree of the voice data may be assigned by further adding the operation history.

Sixth Embodiment

Next, a sixth embodiment of the present disclosure will be described. In the sixth embodiment, the information processing apparatus is incorporated in a part of an endoscope system. Hereinafter, a configuration of an endoscope system according to the sixth embodiment will be described, and then, processing that is executed by the endoscope system according to the sixth embodiment will be described. Furthermore, the same reference numerals will be applied to the same configurations as those of the information processing apparatus 1b according to the fourth embodiment described above, and the detailed description will be suitably omitted.

Configuration of Endoscope System

Figure 23:
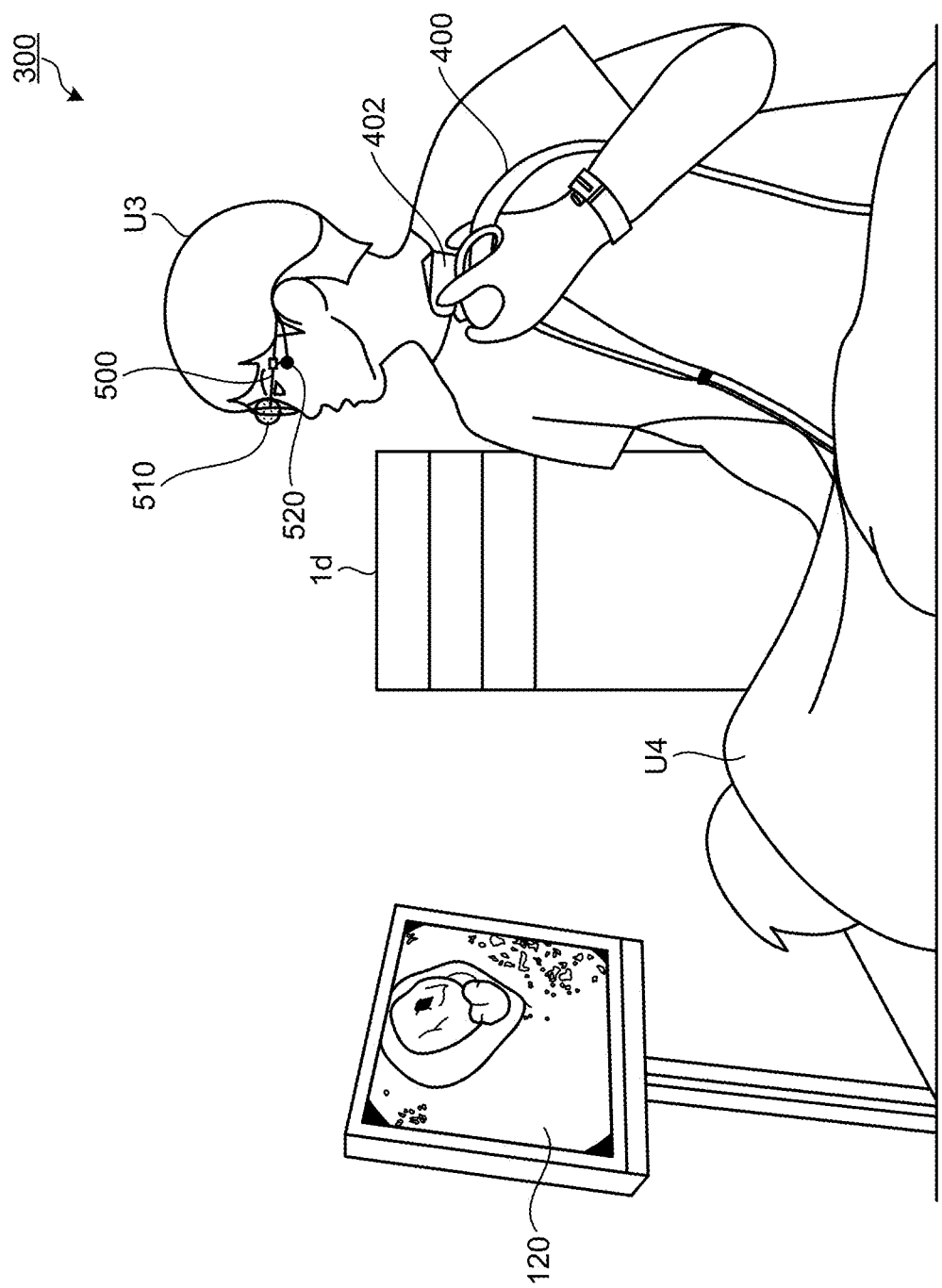
FIG. 23 is a schematic view illustrating a configuration of an endoscope system according to a sixth embodiment of the present disclosure.
Figure 24:
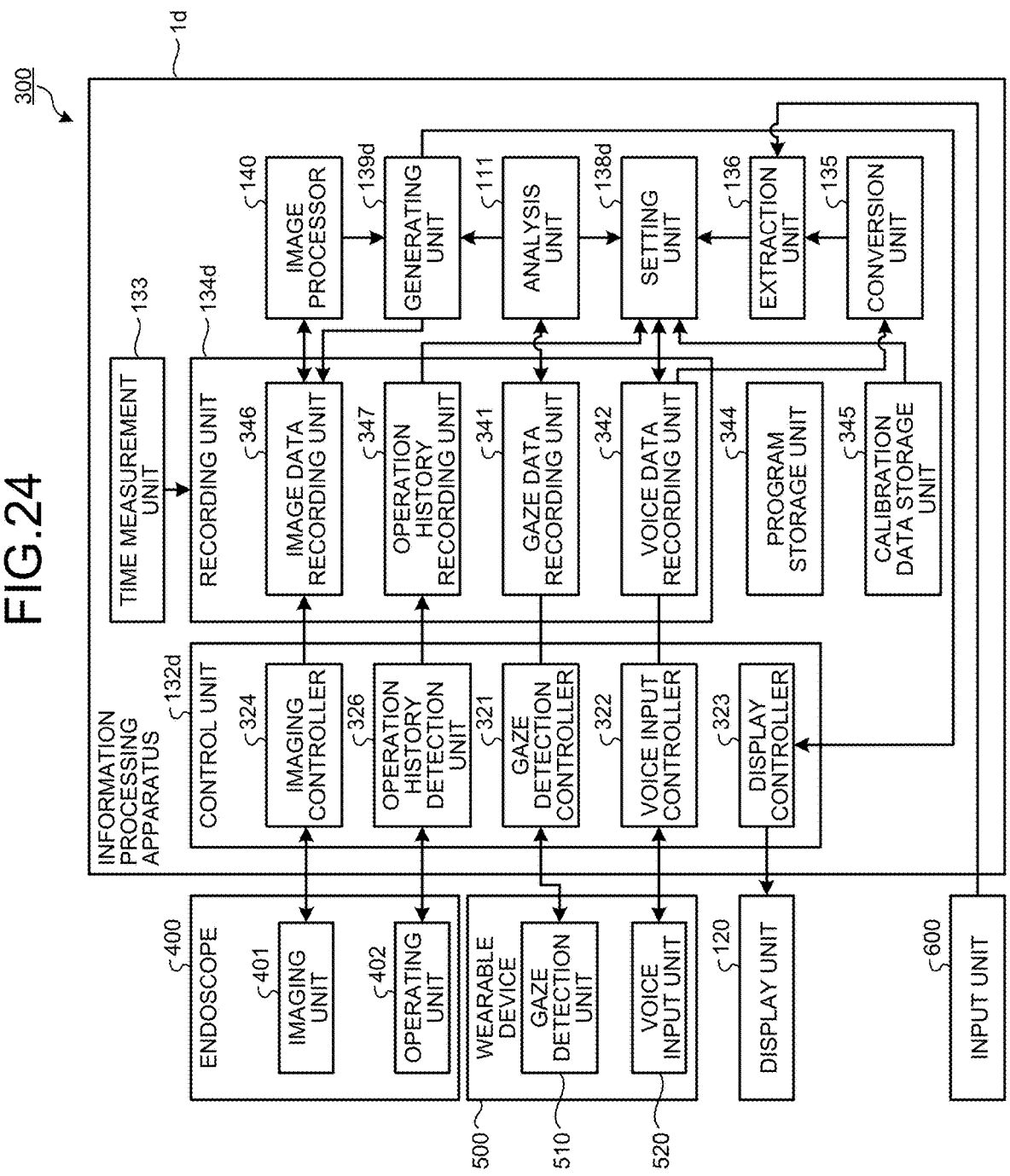
FIG. 24 is a block diagram illustrating a functional configuration of the endoscope system according to the sixth embodiment of the present disclosure.

FIG. 23 is a schematic view illustrating the configuration of the endoscope system according to the sixth embodiment. FIG. 24 is a block diagram illustrating a functional configuration of the endoscope system according to the sixth embodiment.

An endoscope system 300 illustrated in FIG. 23 and FIG. 24 includes the display unit 120, an endoscope 400, a wearable device 500, an input unit 600, and an information processing apparatus 1d.

Configuration of Endoscope

First, the configuration of the endoscope 400 will be described.

The endoscope 400 generates the image data by being inserted into a subject U4 with a user U3 such as a medical doctor or an operator by capturing the inside of the subject U4, and outputs the image data to the information processing apparatus 1d. The endoscope 400 includes an imaging unit 401 and an operating unit 402.

The imaging unit 401 is provided on a tip end portion of an insertion portion of the endoscope 400. The imaging unit 401 generates the image data by capturing the inside of the subject U4, and outputs the image data to the information processing apparatus 1d, under the control of the information processing apparatus 1d. The imaging unit 401 is configured by using an optical system that is capable of changing the observation magnification, an image sensor such as a CMOS or a CCD that generates the image data by receiving the subject image that is formed by the optical system, and the like.

The operating unit 402 receives the input of various operations of the user U3, and outputs an operation signal according to the received various operations to the information processing apparatus 1d.

Configuration of Wearable Device

Next, the configuration of the wearable device 500 will be described.

The wearable device 500 is mounted on the user U3, detects the gaze of the user U3, and receives the input of the voice of the user U3. The wearable device 500 includes a gaze detection unit 510 and a voice input unit 520.

The gaze detection unit 510 is provided in the wearable device 500, generates the gaze data by detecting the attention degree of the gaze of the user U3, and outputs the gaze data to the information processing apparatus 1d. The gaze detection unit 510 has the same configuration as that of the gaze detection unit 220 according to the third embodiment described above, and thus, the detailed configuration will be omitted.

The voice input unit 520 is provided in the wearable device 500, generates the voice data by receiving the input of the voice of the user U3, and outputs the voice data to the information processing apparatus 1d. The voice input unit 520 is configured by using a microphone and the like.

Configuration of Input Unit

The configuration of the input unit 600 will be described.

The input unit 600 is configured by using a mouse, a keyboard, a touch panel, various switches, and the like. The input unit 600 receives the input of various operations of the user U3, and outputs the operation signal according to the received various operation to the information processing apparatus 1d.

Configuration of Information Processing Apparatus

Next, the configuration of the information processing apparatus 1d will be described.

The information processing apparatus 1d includes a control unit 132d, a recording unit 34d, a setting unit 138d, and a generating unit 139d, instead of the control unit 132c, the recording unit 134c, the setting unit 138c, and the generating unit 139 of the information processing apparatus 110c according to the fifth embodiment described above. Further, the information processing apparatus 1d further includes an image processor 140.

The control unit 132d is configured by using a CPU, an FPGA, a GPU, and the like, and controls the endoscope 400, the wearable device 500, and the display unit 120. The control unit 132d includes an operation history detection unit 326, in addition to the gaze detection controller 321, the voice input controller 322, the display controller 323, and the imaging controller 324.

The operation history detection unit 326 detects the contents of the operation of which the input is received by the operating unit 402 of the endoscope 400, and outputs a detection result thereof to the recording unit 134d. Specifically, in a case where an expand switch is operated from the operating unit 402 of the endoscope 400, the operation history detection unit 326 detects the operation contents, and outputs the detection result to the recording unit 134d. Furthermore, the operation history detection unit 326 may detect operation contents of a treatment tool that is inserted into the subject U4 through the endoscope 400, and may output the detection result to the recording unit 134d.

The recording unit 134d is configured by using a volatile memory, a non-volatile memory, a recording medium, and the like. The recording unit 134d further includes an operation history recording unit 347 in addition to the configuration of the recording unit 134c according to the fifth embodiment described above.

The operation history recording unit 347 records the history of the operation with respect to the operating unit 402 of the endoscope 400 that is input from the operation history detection unit 326.

The setting unit 138d assigns the importance degree and the character information that is converted by the conversion unit 135 to the voice data associated with a time axis identical to that of the gaze data, on the basis of the calibration data that is recorded in the calibration data storage unit 345, the attention degree that is analyzed by the analysis unit 111, and the operation history that is recorded in the operation history recording unit 347 to be recorded in the recording unit 134d. Specifically, the setting unit 138d assigns the importance degree (for example, a numerical value) to each frame of the voice data, on the basis of the calibration data that is recorded in the calibration data storage unit 345, the attention degree that is analyzed by the analysis unit 111, and the operation history that is recorded in the operation history recording unit 347 to be recorded in the recording unit 134d. That is, the setting unit 138d performs processing of increasing the importance degree as a coefficient that is set according to the contents of the operation history increases. The setting unit 138d is configured by using a CPU, an FPGA, a GPU, and the like.

The generating unit 139d generates gaze mapping data in which the attention degree that is analyzed by the analysis unit 111 and the character information are associated with an integrated image corresponding to integrated image data that is generated by the image processor 140, and outputs the generated gaze mapping data to the recording unit 134d and the display controller 323.

The image processor 140 generates the integrated image data of a three dimensional image by synthesizing a plurality of image data items that are recorded in the image data recording unit 346, and outputs the integrated image data to the generating unit 139d.

Processing of Endoscope System

Figure 25:
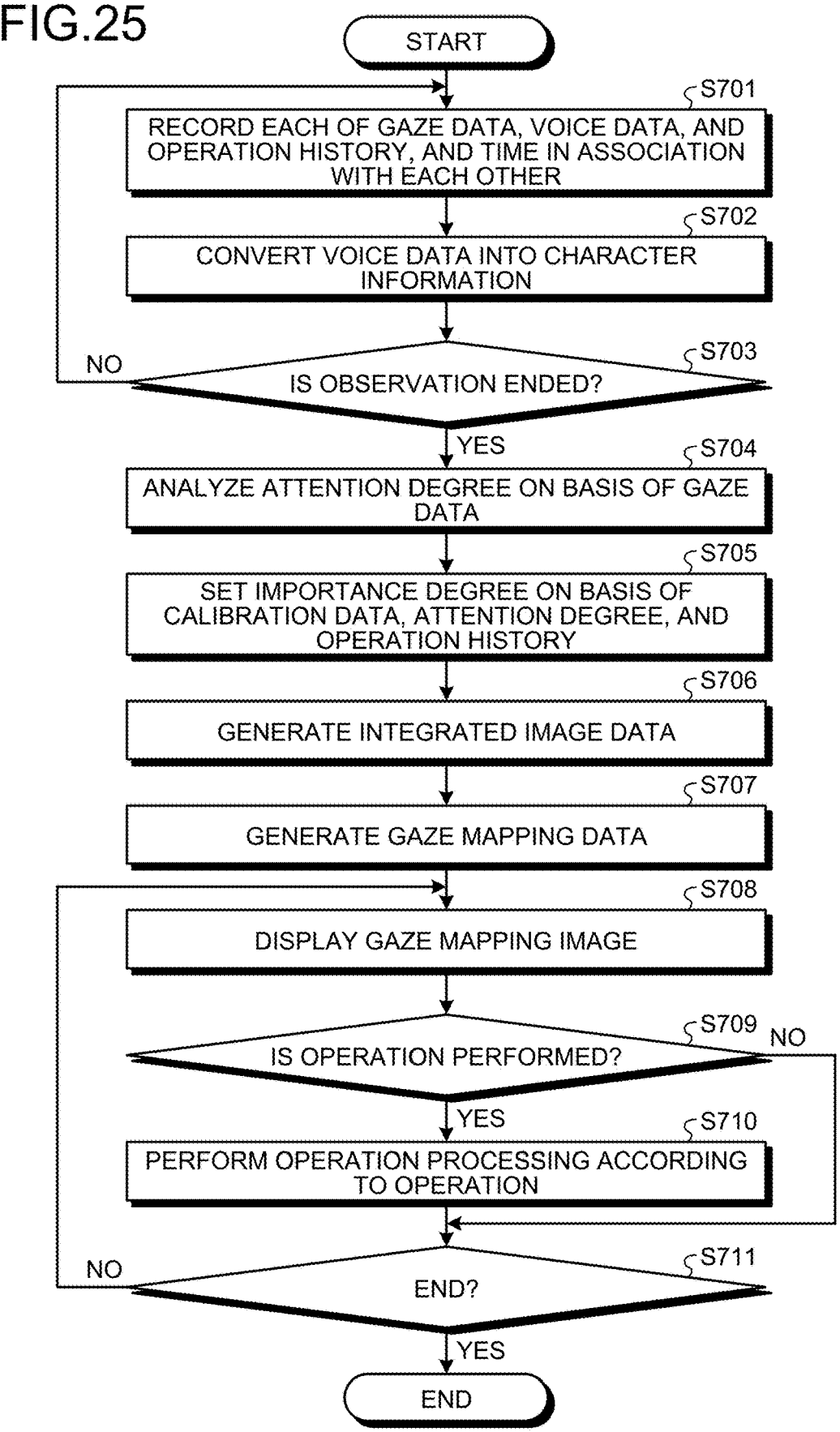
FIG. 25 is a flowchart illustrating an outline of processing that is executed by the endoscope system according to the sixth embodiment of the present disclosure.

Next, processing that is executed by the endoscope system 300 will be described. FIG. 25 is a flowchart illustrating the output of the processing that is executed by the endoscope system 300.

As illustrated in FIG. 25, first, the control unit 132d associates each of the gaze data that is generated by the gaze detection unit 510, the voice data that is generated by the voice input unit 520, and the operation history that is detected by the operation history detection unit 326 with the time that is measured by the time measurement unit 133 to be recorded in the gaze data recording unit 341, the voice data recording unit 342, and the operation history recording unit 347 (Step S701). After Step S701, the endoscope system 300 proceeds to Step S702 described below.

Step S702 to Step S704 respectively correspond to Step S503 to Step S505 of FIG. 17 described above. After Step S704, the endoscope system 300 proceeds to Step S705.

In Step S705, the setting unit 138d assigns the importance degree and the character information that is converted by the conversion unit 135 to the voice data associated with a time axis identical to the gaze data, on the basis of the calibration data that is recorded in the calibration data storage unit 345, the attention degree that is analyzed by the analysis unit 111, and the operation history that is recorded in the operation history recording unit 347 to be recorded in the recording unit 34d.

Figure 26:
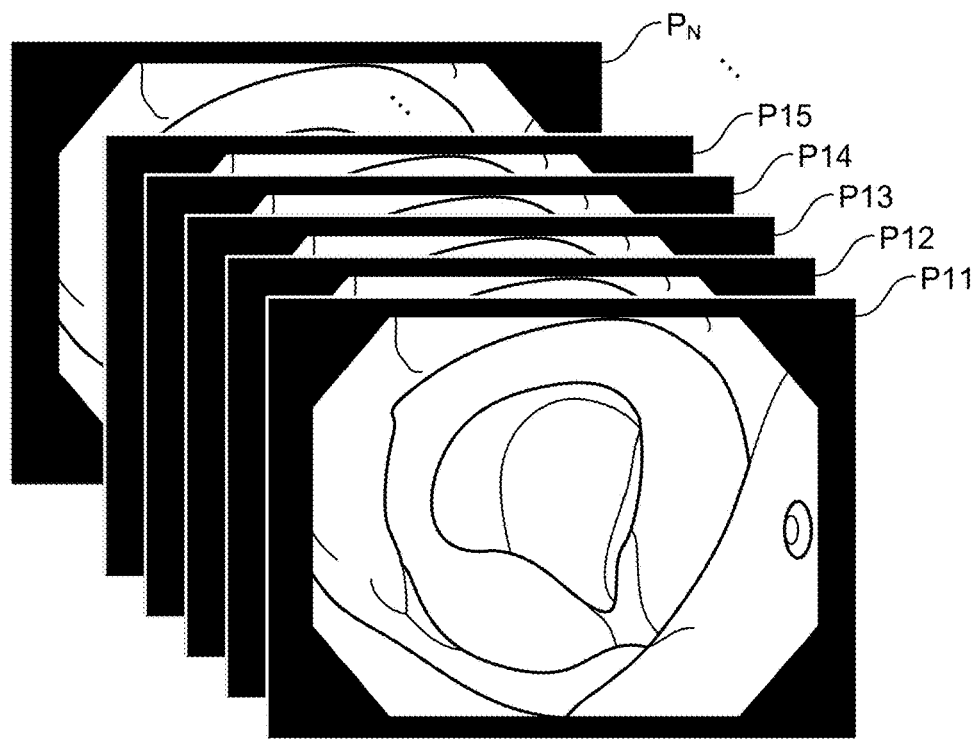
FIG. 26 is a diagram schematically illustrating an example of a plurality of images corresponding to a plurality of image data items that is recorded in an image data recording unit according to the sixth embodiment of the present disclosure.
Figure 27:
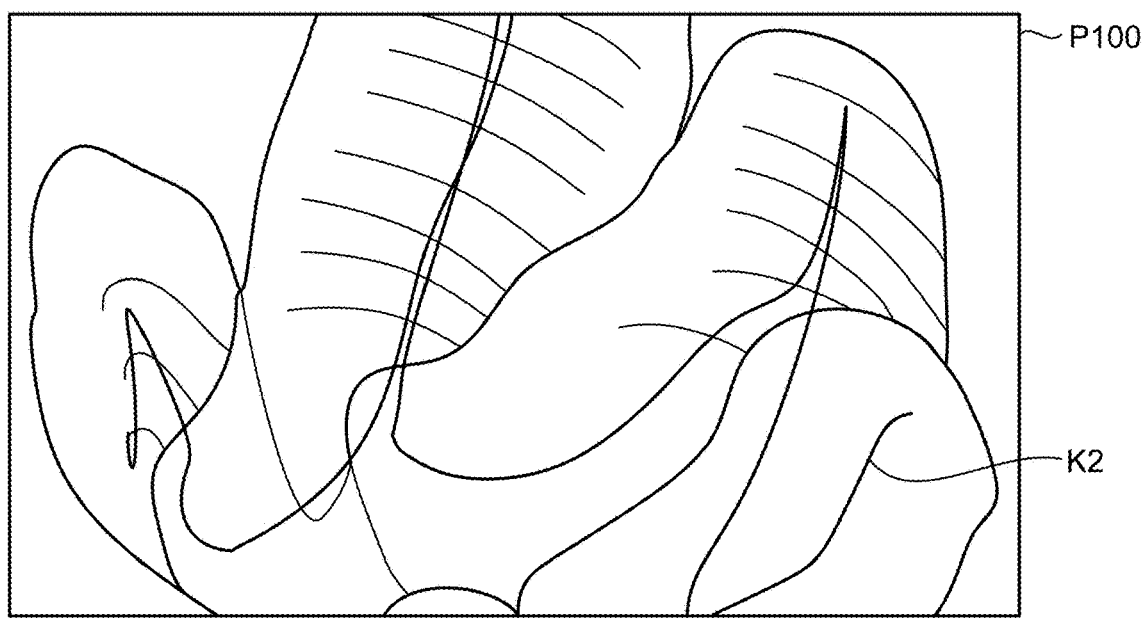
FIG. 27 is diagram illustrating an example of an integrated image corresponding to integrated image data that is generated by an image processor according to the sixth embodiment of the present disclosure.

Subsequently, the image processor 140 generates the integrated image data of the three dimensional image by synthesizing the plurality of image data items that are recorded in the image data recording unit 346, and outputs the integrated image data to the generating unit 139d (Step S706). FIG. 26 is a diagram schematically illustrating an example of a plurality of images corresponding to the plurality of image data items that are recorded in the image data recording unit 346. FIG. 27 is a diagram illustrating an example of an integrated image corresponding to the integrated image data that is generated by the image processor 140. As illustrated in FIG. 26 and FIG. 27, the image processor 140 generates an integrated image P100 corresponding to the integrated image data by synthesizing a plurality of temporally continuous image data items P11 to $P_N$ (N=Integer).

After that, the generating unit 139d generates the gaze mapping data in which the attention degree that is analyzed by the analysis unit 111, the gaze and the character information are associated with the integrated image P100 corresponding to the integrated image data that is generated by the image processor 140, and outputs the generated gaze mapping data to the recording unit 34d and the display controller 323 (Step S707). In this case, the generating unit 139d may associate the operation history with the integrated image P100 corresponding to the integrated image data that is generated by the image processor 140, in addition to the attention degree that is analyzed by the analysis unit 111, a gaze K2, and the character information. After Step S707, the endoscope system 300 proceeds to Step S708 described below.

Step S708 to Step S711 respectively correspond to Step S508 to Step S511 of FIG. 17 described above.

According to the sixth embodiment described above, the setting unit 138d assigns the importance degree and the character information that is converted by the conversion unit 135 to the voice data associated with a time axis identical to that of the gaze data, on the basis of the attention degree that is analyzed by the analysis unit 111 and the operation history that is recorded in the operation history recording unit 347 to be recorded in the recording unit 34d, and thus, assigns importance degree based on the operation history and the attention degree to the voice data, and therefore, it is possible to grasp an important period of the voice data to which the operation contents and the attention degree are input.

In addition, in the sixth embodiment, the endoscope system is described, but for example, a capsule type endoscope, a video microscope capturing a subject, a mobile phone having a capturing function, and a tablet type terminal having a capturing function can also be applied.

In addition, in the sixth embodiment, the endoscope system including a flexible endoscope is described, but an endoscope system including a rigid endoscope, and an endoscope system including an industrial endoscope can also be applied.

In addition, in the sixth embodiment, the endoscope system including the endoscope that is inserted into the subject is described, but a sinus endoscope, and an endoscope such as an electrosurgical knife or an inspection probe can also be applied.

Seventh Embodiment

Next, a seventh embodiment of the present disclosure will be described. In the third embodiment to the sixth embodiment described above, a case where there is one user is assumed, but in the seventh embodiment, a case where there are two or more users is assumed. Further, in the seventh embodiment, the information processing apparatus is incorporated in an information processing system in which an image is browsed by a plurality of users. Hereinafter, the configuration of a browsing system according to the seventh embodiment will be described, and then, processing that is executed by the information processing system according to the seventh embodiment will be described. Furthermore, the same reference numerals will be applied to the same configurations as those of the information processing apparatus 1b according to the fourth embodiment described above, and the detailed description will be suitably omitted.

Configuration of Information Processing System

Figure 28:
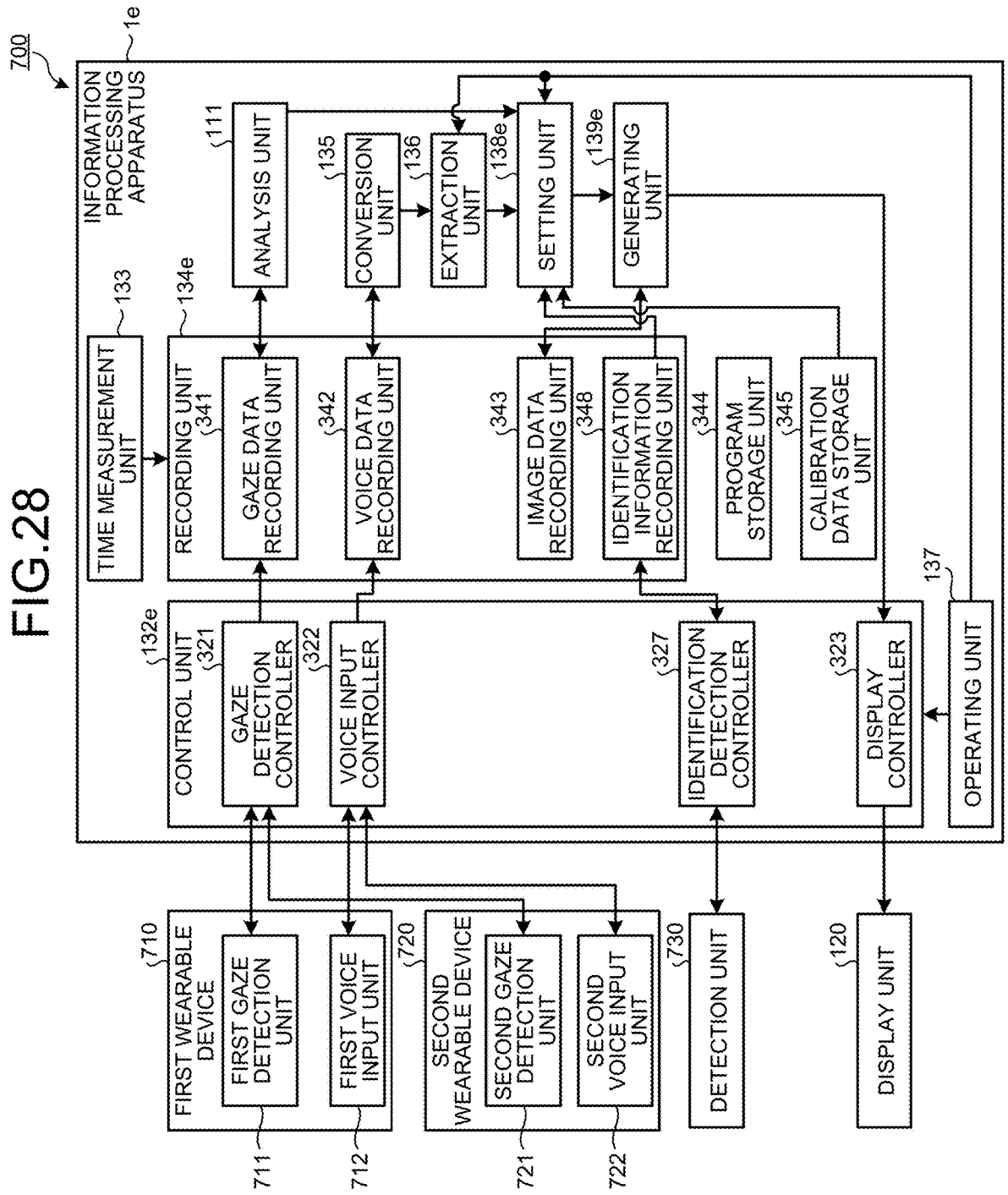
FIG. 28 is a block diagram illustrating a functional configuration of an information processing system according to a seventh embodiment of the present disclosure.

FIG. 28 is a block diagram illustrating a functional configuration of the information processing system according to the seventh embodiment. An information processing system 700 illustrated in FIG. 28 includes the display unit 120, a first wearable device 710, a second wearable device 720, a detection unit 730, and an information processing apparatus 1e.

Configuration of First Wearable Device

First, the configuration of the first wearable device 710 will be described.

The first wearable device 710 is mounted on the user, detects the gaze of the user, and receives the input of the voice of the user. The first wearable device 710 includes a first gaze detection unit 711 and a first voice input unit 712. The first gaze detection unit 711 and the first voice input unit 712 have the same configuration as that of the gaze detection unit 510 and the voice input unit 520 according to the sixth embodiment described above, and thus, the detailed configuration will be omitted.

Configuration of Second Wearable Device

Next, the configuration of the second wearable device 720 will be described.

The second wearable device 720 has the same configuration as that of the first wearable device 710 described above, is mounted on the user, detects the gaze of the user, and receives the input of the voice of the user. The second wearable device 720 includes a second gaze detection unit 721 and a second voice input unit 722. The second gaze detection unit 721 and the second voice input unit 722 have the same configuration as that of the gaze detection unit 510 and the voice input unit 520 according to the sixth embodiment described above, and thus, the detailed configuration will be omitted.

Configuration of Detection Unit

Next, the configuration of the detection unit 730 will be described.

The detection unit 730 detects identification information of identifying each of the plurality of users, and outputs a detection result to the information processing apparatus 1e. The detection unit 730 detects the identification information of the user from an IC card in which the identification information (for example, an ID, a name, or the like) of identifying each of the plurality of users is recorded, and outputs the detection result to the information processing apparatus 1e. The detection unit 730, for example, is configured by using a card reader that reads the IC card. Furthermore, the detection unit 730 may identify the user by using a feature point of the face of the user that is set in advance and known pattern matching, with respect to the image corresponding to the image data generated by capturing the face of the plurality of users, and may output an identification result to the information processing apparatus 1e. It is obvious that the detection unit 730 may identify the user on the basis of a signal that is input according to the operation from the operating unit 137, and may output the identification result to the information processing apparatus 1e.

Configuration of Information Processing Apparatus

Next, the configuration of the information processing apparatus 1e will be described.

The information processing apparatus 1e includes a control unit 132e, a recording unit 134e, and a setting unit 138e, instead of the control unit 132d, the recording unit 134d, and the setting unit 138d of the information processing apparatus 1d according to the sixth embodiment described above.

The control unit 132e is configured by using a CPU, an FPGA, a GPU, and the like, and controls the first wearable device 710, the second wearable device 720, the detection unit 730, and the display unit 120. The control unit 132e includes an identification detection controller 327, in addition to the gaze detection controller 321, the voice input controller 322, and the display controller 323.

The identification detection controller 327 controls the detection unit 730, identifies each of the plurality of users on the basis of an acquisition result acquired by the detection unit 730, and outputs the identification result to the recording unit 134e.

The recording unit 134e is configured by using a volatile memory, a non-volatile memory, a recording medium, and the like. The recording unit 134e further includes an identification information recording unit 348 in addition to the configuration of the configuration of the recording unit 134c according to the fourth embodiment described above.

The identification information recording unit 348 records the identification information of each of the plurality of users that is input from the identification detection controller 327.

The setting unit 138e assigns the importance degree and the character information that is converted by the conversion unit 135 to the voice data associated with a time axis identical to that of the gaze data at each predetermined time interval, on the basis of the calibration data of each user that is recorded in the calibration data storage unit 345, each analysis result that is analyzed by the analysis unit 111, the character information that is extracted by the extraction unit 136, and the identification information that is recorded in the identification information recording unit 348 to be recorded in the recording unit 134e. Further, the setting unit 138e performs weighting of the importance degree according to the identification information of each of the users that is recorded in the identification information recording unit 348. That is, the setting unit 138e performs processing of increasing the importance degree as the user is important (for example, a rank set according to an official position).

Processing of Information Processing System

Figure 29:
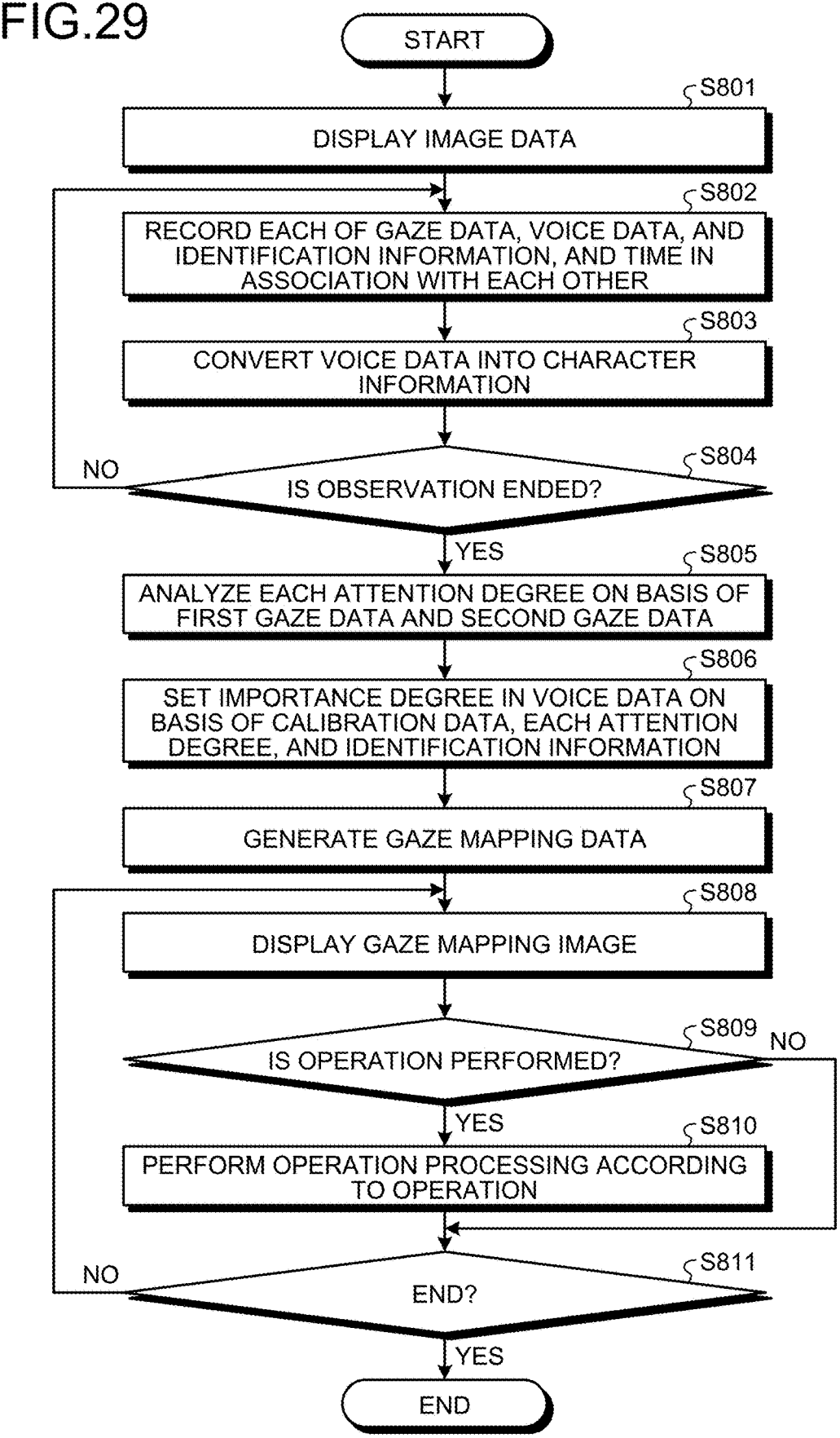
FIG. 29 is a flowchart illustrating an outline of processing that is executed by the information processing system according to the seventh embodiment of the present disclosure.

Next, processing that is executed by the information processing system 700 will be described. FIG. 29 is a flowchart illustrating the outline of the processing that is executed by the information processing system 700.

As illustrated in FIG. 29, the display controller 323 allows the display unit 120 to display the image corresponding to the image data that is recorded in the image data recording unit 343 (Step S801).

Subsequently, the control unit 132e associates each of the gaze data that is generated by each of the first wearable device 710 and the second wearable device 720, the voice data, and the identification information that is acquired by the detection unit 730 with the time that is measured by the time measurement unit 133 to be recorded in the gaze data recording unit 341, the voice data recording unit 342, and the identification information recording unit 348 (Step S802). After Step S802, the information processing system 700 proceeds to Step S803.

Step S803 and Step S804 respectively correspond to Step S503 and Step S504 of FIG. 17 described above. After Step S804, the information processing system 700 proceeds to Step S805 described below.

In Step S805, the analysis unit 111 analyzes the attention degree of the gaze of each of the users, on the basis of first gaze data that is generated by the first wearable device 710 and second gaze data that is generated by the second wearable device 720.

Subsequently, the setting unit 138e assigns the importance degree and the character information that is converted by the conversion unit 135 to each of the first voice data and the second voice data associated with a time axis identical to that of the gaze data, on the basis of each attention degree that is analyzed by the analysis unit 111 at each predetermined time interval, and the identification information that is recorded in the identification information recording unit 348 to be recorded in the recording unit 134e (Step S806).

Step S807 to Step S811 respectively correspond to Step S507 to Step S511 of FIG. 17 described above.

According to the seventh embodiment described above, the setting unit 138e assigns the importance degree and the character information that is converted by the conversion unit 135 to each of the first voice data and the second voice data associated with a time axis identical to that of the gaze data, on the basis of the attention degree of each of the users that is analyzed by the analysis unit 111, and the identification information that is recorded in the identification information recording unit 348 to be recorded in the recording unit 134e, and thus, the identification information and the importance degree based on the attention degree are assigned to the first voice data or the second voice data, and thus, it is possible to grasp an important period of the voice data to which the attention degree according to the user is added.

Furthermore, in the seventh embodiment, the setting unit 138e assigns the importance degree and the character information that is converted by the conversion unit 135 to each of the first voice data and the second voice data associated with a time axis identical to that of the gaze data to be recorded in the recording unit 134e, on the basis of the attention degree of each of the users analyzed by the analysis unit 111 and the identification information of each of the users that is recorded in the identification information recording unit 348, but is not limited thereto, and for example, may detect the position of each of the plurality of users, and may assign the importance degree and the character information that is converted by the conversion unit 135 to each of the first voice data and the second voice data, on the basis of a detection result and the attention degree of each of the users to be recorded in the recording unit 134e.

Other Embodiments

A plurality of constituents disclosed in the first embodiment to the seventh embodiment described above are suitably combined, and thus, various inventions can be made. For example, some constituents of all of the constituents described in the first embodiment to the seventh embodiment described above may be deleted. Further, the constituents described in the first embodiment to the seventh embodiment described above may be suitably combined.

In addition, in the first embodiment to the seventh embodiment, the "unit" that has been described above can be read as a "section", a "circuit", or the like. For example, the control unit can be read as a control section or a control circuit.

In addition, a program that is executed in the information processing apparatus according to the first embodiment to the seventh embodiment is file data in an installable format or an executable format, and is provided by being recorded in a recording medium that can be read by a computer, such as a CD-ROM, a flexible disk (FD), a CD-R, a digital versatile disk (DVD), a USB medium, and a flash memory.

In addition, the program that is executed in the information processing apparatus according to the first embodiment to the seventh embodiment may be stored on a computer that is connected to a network such as the internet, and may be provided by being downloaded through the network. Further, the program that is executed in the information processing apparatus according to the first embodiment to the seventh embodiment may be provided or distributed through a network such as the internet.

In addition, in the first embodiment to the seventh embodiment, the signal is transmitted from various devices through a transmission cable, but for example, it is not necessary to transmit the signal in a wired manner, and the signal may be transmitted in a wireless manner. In this case, it is sufficient that the signal is transmitted from each of the devices, according to a predetermined wireless communication standard (for example, Wi-Fi (Registered Trademark) or Bluetooth (Registered Trademark)). It is obvious that wireless communication may be performed according to other wireless communication standards.

Furthermore, herein, in the description of the flowchart, an anteroposterior relationship of the pieces of processing between steps is explicitly described by using the expression of "first", "after that", "subsequently", and the like, but the order of processing that is necessary for carrying out the present invention is not uniquely determined by the expression. That is, the order of the processing in the flowchart described herein can be changed without contradiction.

According to the present disclosure, an effect is obtained in which the time lag between the attention point of the gaze and the time when the voice is output can be corrected.

As described above, some embodiments of the present invention have been described in detail on the basis of the drawings, but the embodiments are merely an example, and it is possible to carry out the present invention not only in the aspects described at the beginning of the present invention but also in other forms in which various modifications and improvements are made on the basis of the knowledge of a person skilled in the art.

What is claimed is:

1. An information processing apparatus, comprising:
  a display that displays a correction image in which a coordinate position of each of a plurality of observation points is set;
  a first memory that records correction voice data in which a voice to be pronounced at each of the plurality of observation points of the correction image is set;
  a gaze detector that generates gaze data by continuously detecting a gaze of a user;

a voice input device that generates voice data associated with a time axis identical to that of the gaze data by receiving input of a voice of the user; and a hardware processor configured to,
analyze a attention period in which a attention degree of the gaze of the user with respect to each of the plurality of observation points is greater than or equal to a predetermined value, on the basis of the gaze data that is generated by the gaze detector, set a period in which the voice is pronounced with respect to the voice data as an important voice period, on the basis of the correction voice data that is recorded in the first memory, and generate calibration data of the user on the basis of a time lag between the attention period and the important voice period to be recorded in a second memory.

2. The information processing apparatus according to claim 1,
wherein the hardware processor is further configured to calculate the time lag between the attention period and the important voice period a plurality of times, and generate the calibration data on the basis of statistical characteristics of a plurality of calculation results.

3. The information processing apparatus according to claim 1,
wherein the calibration data relates to a time difference based on a start time or an end time of any one of the gaze data and the voice data.

4. The information processing apparatus according to claim 1,
wherein the calibration data relates to a length of a period based on any one of the gaze data and the voice data.

5. The information processing apparatus according to claim 1,
wherein the hardware processor is further configured to generate a time lag between a start time of the attention period and a start time of the important voice period, or a time lag between an end time of the attention period and an end time of the important voice period, as the calibration data.

6. The information processing apparatus according to claim 1,
wherein the hardware processor is further configured to further set a period in which a keyword designated in advance is pronounced according to an operation signal that is input externally, as the important voice period.

7. The information processing apparatus according to claim 1,
wherein the gaze detector generates new gaze data by continuously detecting the gaze of the user after the hardware processor generates the calibration data, the voice input device generates new voice data associated with a time axis identical to that of the new gaze data by receiving the input of the voice of the user after the hardware processor generates the calibration data, and the hardware processor is further configured to,
analyze a new attention period in which a new attention degree of the gaze of the user is greater than or equal to a predetermined value, on the basis of the new gaze data, and correct a time lag between the new attention period and a new important voice period included in the new voice data, on the basis of the calibration data.

8. The information processing apparatus according to claim 7,
wherein the hardware processor is further configured to assign an importance degree according to the new attention degree with respect to the new voice data by using the new attention degree and the calibration data to be recorded in the second memory.

9. The information processing apparatus according to claim 7,
wherein the hardware processor is further configured to set a pronunciation period in which the new voice data is pronounced with respect to the new voice data, and assign an importance degree according to the new attention degree with respect to the new voice data by using the pronunciation period, the new attention degree, and the calibration data to be recorded in the second memory.

10. The information processing apparatus according to claim 7,
wherein the hardware processor is further configured to set a period in which a predetermined keyword in the new voice data is pronounced as anew important pronunciation period, and assign an importance degree according to the new important pronunciation period with respect to the new gaze data by using the new important pronunciation period and the calibration data to be recorded in the second memory.

11. The information processing apparatus according to claim 7,
wherein the hardware processor is further configured to set a period in which a predetermined keyword in the new voice data is pronounced, as a new important pronunciation period, and assign an importance degree according to the important pronunciation period with respect to the new gaze data by using the new attention period, the new important pronunciation period, and the calibration data to be recorded in the second memory.

12. The information processing apparatus according to claim 8,
wherein the hardware processor is further configured to analyze the attention degree by detecting any one of a moving speed of the gaze, a moving distance of the gaze within a predetermined time, and a residence time of the gaze within a prescribed area.

13. The information processing apparatus according to claim 8,
wherein the hardware processor is further configured to generate gaze mapping data in which the new attention degree that is analyzed and coordinate information of the new attention degree are associated with an image corresponding to image data that is input externally.

14. The information processing apparatus according to claim 13,
wherein the hardware processor is further configured to,
further analyze a locus of the gaze of the user, on the basis of the new gaze data, and
generate the gaze mapping data by further associating the analyzed locus with the image.

15. The information processing apparatus according to claim 13,
wherein the hardware processor is further configured to,
convert the new voice data into character information, and
generate the gaze mapping data by further associating the character information with the coordinate information.

16. The information processing apparatus according to claim 13, further comprising:
a microscope including an eyepiece portion that is capable of changing an observation magnification of observing a specimen, and allows the user to observe an observation image of the specimen; and
an imaging sensor connected to the microscope, the imaging sensor generating image data by capturing the observation image of the specimen that is formed by the microscope,
wherein the gaze detector is provided in the eyepiece portion of the microscope, and
the hardware processor is further configured to perform weighting of the importance degree according to the observation magnification.

17. The information processing apparatus according to claim 13, further comprising:
an endoscope including an imaging sensor that is provided on a tip end portion of an insertion portion capable of being inserted into a subject, and generates image data by capturing an in-vivo image of the subject, and an operating unit that receives input of various operations for changing a field of view.

18. The information processing apparatus according to claim 8,
wherein the hardware processor is further configured to generate data in which the new gaze data including the new attention degree corresponding to the new attention period, and the new voice data including the importance degree corresponding to the new important voice period are associated with each other.

19. An information processing method, comprising:
displaying a correction image in which a coordinate position of each of a plurality of observation points is set;
generating gaze data by continuously detecting a gaze of a user;
generating voice data associated with a time axis identical to that of the gaze data by receiving input of a voice of the user;
analyzing an attention period in which an attention degree of the gaze of the user with respect to each of the plurality of observation points is greater than or equal to a predetermined value, on the basis of the generated gaze data;
setting a time when the voice is pronounced with respect to the voice data as an important voice period, on the basis of correction voice data recorded in a first memory that records the correction voice data in which a voice to be pronounced at each of the plurality of observation points of the correction image is set; and
generating a time lag between the attention period and the important voice period as calibration data of the user to be recorded in a second memory.

20. A non-transitory computer readable recording medium that records a program of allowing an information processing apparatus to execute:
displaying a correction image in which a coordinate position of each of a plurality of observation points is set;
generating gaze data by continuously detecting a gaze of a user;
generating voice data associated with a time axis identical to that of the gaze data by receiving input of a voice of the user;
analyzing an attention period in which an attention degree of the gaze of the user with respect to each of the plurality of observation points is greater than or equal to a predetermined value, on the basis of the generated gaze data;
setting a time when the voice is pronounced with respect to the voice data as an important voice period, on the basis of correction voice data recorded in a first memory that records the correction voice data in which a voice to be pronounced at each of the plurality of observation points of the correction image is set; and
generating a time lag between the attention period and the important voice period as calibration data of the user to be recorded in a second memory.

* * * * *